(12) United States Patent
Levin et al.

(10) Patent No.: US 12,702,481 B2
(45) Date of Patent: Aug. 11, 2026

(54) VIRTUAL SIMULATOR FOR PLANNING AND EXECUTING ROBOTIC STEERING OF A MEDICAL INSTRUMENT

(71) Applicant: XACT ROBOTICS LTD., Caesarea (IL)

(72) Inventors: Chen Levin, Ramat Gan (IL); Nir Shachar, Shimshit (IL); Ido Roth, Pardes Hanna (IL); Danna Perlman, Haifa (IL); Moran Shochat, Zikron Ya'aqov (IL)

(73) Assignee: XACT ROBOTICS LTD., Caesarea (IL)

( * ) Notice: Subject to any disclaimer, the term of this patent is extended or adjusted under 35 U.S.C. 154(b) by 483 days.

(21) Appl. No.: 18/038,134

(22) PCT Filed: Nov. 28, 2021

(86) PCT No.: PCT/IL2021/051415
§ 371 (c)(1),
(2) Date: May 22, 2023

(87) PCT Pub. No.: WO2022/113085
PCT Pub. Date: Jun. 2, 2022

(65) Prior Publication Data
US 2023/0363821 A1 Nov. 16, 2023

Related U.S. Application Data

(60) Provisional application No. 63/118,939, filed on Nov. 29, 2020.

(51) Int. Cl.
*A61B 34/00* (2016.01)
*A61B 34/10* (2016.01)
(Continued)

(52) U.S. Cl.
CPC ............. *A61B 34/10* (2016.02); *A61B 34/32* (2016.02); *A61B 2034/102* (2016.02);
(Continued)

(58) Field of Classification Search
CPC ... A61B 34/10; A61B 34/32; A61B 2034/102; A61B 2034/105; A61B 2034/107;
(Continued)

(56) References Cited

U.S. PATENT DOCUMENTS 8,348,861 B2 1/2013 Glozman et al.
8,663,130 B2 3/2014 Neubach et al.
(Continued)

FOREIGN PATENT DOCUMENTS

WO 2021105992 A1 6/2021
WO 2021111445 A1 6/2021
(Continued)

OTHER PUBLICATIONS

PCT International Search Report for International Application No. PCT/IL2021/051415, mailed Mar. 8, 2022, 7pp.
(Continued)

*Primary Examiner* — Ian Jen
(74) *Attorney, Agent, or Firm* — The Roy Gross Law Firm, LLC; Roy D. Gross

(57) ABSTRACT

Provided are simulation systems and methods for simulation of planning and executing a procedure for robotic insertion and/or steering of a medical instrument toward an internal target.

20 Claims, 12 Drawing Sheets

(51) Int. Cl.
*A61B 34/32* (2016.01)
*A61B 34/30* (2016.01)

(52) U.S. Cl.
CPC ... *A61B 2034/105* (2016.02); *A61B 2034/107* (2016.02); *A61B 2034/301* (2016.02); *A61B 2034/302* (2016.02)

(58) Field of Classification Search
CPC ........ A61B 2034/301; A61B 2034/302; A61B 2034/2065; A61B 2090/374; A61B 2090/3762; A61B 34/35; A61B 2034/101; G09B 23/285; G09B 23/28
See application file for complete search history.

(56) References Cited

U.S. PATENT DOCUMENTS 10,507,067 B2 12/2019 Glozman et al.
10,639,107 B2 5/2020 Glozman et al.
11,083,488 B2 8/2021 Galili et al.
11,103,277 B2 8/2021 Arnold et al.
2004/0009459 A1 1/2004 Anderson et al.
2004/0161731 A1* 8/2004 Arington .................. G09B 7/04
434/262
2013/0072784 A1 3/2013 Velusamy
2016/0070436 A1 3/2016 Thomas et al.
2018/0098813 A1* 4/2018 Nesichi .................. G09B 23/28
2019/0005848 A1 1/2019 Garcia Kilroy et al.
2019/0080515 A1 3/2019 Geri et al.
2019/0125397 A1 5/2019 Arnold et al.
2019/0290372 A1 9/2019 Arnold et al.
2019/0307362 A1* 10/2019 Piron .................. A61B 5/0042
2021/0228311 A1 7/2021 Galili et al.
2021/0259776 A1* 8/2021 Upadrasta .............. A61B 34/10
2022/0293014 A1* 9/2022 Fisher .................. G09B 23/285

FOREIGN PATENT DOCUMENTS

WO 2021214750 A1 10/2021
WO 2021214751 A1 10/2021
WO 2021214754 10/2021

OTHER PUBLICATIONS

PCT Written Opinion for International Application No. PCT/IL2021/051415, mailed Mar. 8, 2022, 7pp.
PCT International Preliminary Report on Patentability for International Application No. PCT/IL2021/051415, issued May 30, 2023, 8pp.

* cited by examiner

70

VIRTUAL SIMULATOR FOR PLANNING AND EXECUTING ROBOTIC STEERING OF A MEDICAL INSTRUMENT

This application is a National Phase of PCT Patent Application No. PCT/IL2021/051415 having International filing date of Nov. 28, 2021, which claims the benefit of priority of U.S. Provisional Patent Application No. 63/118,939, filed Nov. 29, 2022, the contents of which are all incorporated herein by reference in their entirety.

FIELD OF THE INVENTION

The present disclosure relates to computer-implemented methods and systems for simulating the planning and execution of medical instrument insertion and/or steering toward a desired target in a body of a subject using an automated (robotic) medical system. More specifically, the disclosed methods and systems relate to training users how to plan and monitor robotic insertion and/or steering of a medical instrument during image-guided medical procedures.

BACKGROUND

Various diagnostic and therapeutic procedures used in clinical practice involve the insertion and of medical tools, such as needles and catheters, percutaneously to a subject's body, and in many cases further involve the steering of the medical tools within the body, to reach the target region. The target region can be any internal body region, including, a lesion, tumor, organ or vessel. Examples of procedures requiring insertion of such medical tools include vaccinations, blood/fluid sampling, regional anesthesia, tissue biopsy, catheter insertion, cryogenic ablation, electrolytic ablation, brachytherapy, neurosurgery, deep brain stimulation, various minimally invasive surgeries, and the like.

The guidance and steering of medical tools, such as needles, in soft tissue is a complicated task that requires good three-dimensional coordination, knowledge of the patient's anatomy and a high level of experience. Image-guided automated (e.g., robotic) systems have been proposed for performing these functions.

Some automated insertion systems are based on manipulating robotic arms and some utilize a body-mountable robotic device. Some systems are guiding systems that assist the physician in selecting an insertion point and in aligning the medical instrument with the insertion point and with the target, and some systems are insertion/steering systems that also automatically insert the instrument towards the target.

The operation of such automated medical devices in various medical procedures requires training and practice to improve the capabilities of the user and increase the safety, efficiency and accuracy of the medical procedure.

Thus, there is a need in the art for simulators that can at least partially simulate a medical procedure of planning and/or executing insertion/steering of a medical instrument to a target region by an automated medical device, for training, education and/or evaluation purposes.

SUMMARY

According to some embodiments, the present disclosure is directed to systems and methods for simulation of insertion and/or steering of medical instruments toward a target in a subject's body by an automated medical device. Such simulation methods and simulator systems may be used for various purposes, including, for example, training, learning, practicing, evaluating user performance, increasing efficiency, safety and efficacy of the medical procedures involved, quality assurance, quality testing, validation and verification of the clinical automated system, e.g., by setting up a variety of test cases, such as regression-type cases, in which the results are compared to the expected results to ensure correctness, or new situations in which system performance is to be tested, and the like.

According to some embodiments, the present disclosure is directed to systems and methods for simulation of planning a trajectory for a medical instrument from an entry point toward a desired target and simulation of the execution of the planned trajectory. The simulation methods and systems disclosed herein may include, inter alia, planning a trajectory for a medical instrument within a body of the subject, to facilitate the safe and accurate reaching of the medical instrument to an internal target region within the subject's body, by the most efficient and safe route, in a virtual setting.

According to some embodiments, the systems and methods provided herein allow the simulation of a selected medical procedure in a virtual setting, whereby the methods and systems are configured to receive input from a user (a trainee, such as a physician), regarding one or more variables or parameters (such as, for example, at least one of the medical procedure to be executed and/or a region of interest (e.g., lung, liver, kidney, lymph node, etc.) and various other related variables or parameters, such as, but not limited to: type of medical instrument to be used, a target point/region, an entry point, one or more obstacles, one or more checkpoints along the trajectory, and the like, or combinations thereof.

According to some embodiments, the simulation systems and methods disclosed herein are advantageous as they allow a user to train, practice and/or learn the operation of an automated medical system, including an automated (robotic) medical device for insertion and/or steering of a medical instrument in a virtual environment, which not only mimics or imitates real-time and live procedures in an accurate manner, but is further capable of providing versatile scenarios, based at least in part, on one or more values or parameters selected by the user. According to some embodiments, the simulation systems and methods disclosed herein are configured to teach and train users on different considerations and variables of medical procedures (e.g., interventional procedures), how to operate the automated system to best address the different considerations and variables, how to operate the automated system to mitigate possible complications which may occur during a medical procedure, what the limitations of the automated system are, etc.

According to some embodiments, the simulator systems and method disclosed herein allow a user to train, practice, learn, be evaluated, and the like, in a virtual environment, which simulates actual procedures of inserting and/or steering a medical instrument by an automated medical device, to a region of interest in a body of a subject, according to a planned and, optionally, an updated trajectory. As further detailed herein, various simulation parameters can be at least partially selected automatically (in a planned or random fashion) or can at least partially be selected by the user.

According to some embodiments, the simulation methods and systems disclosed herein may include generating or presenting one or more of an image, a scan, an image frame, a set of images (generally referred to as "image-view), a presentation and an animation based on or related to one or more parameters of the simulation session. A simulation session may include one or more portions of a procedure for planning and executing insertion and/or steering of a medical instrument by an automated medical device to a target within a body of a subject.

According to some embodiments, the simulation methods disclosed herein are computerized and may be executed by a suitable processing and/or controlling unit, which may be harbored in a suitable simulation system. The simulation system (also referred to as "simulator") may further include any suitable operational units, including, but not limited to: a display, a user interface, a memory module, a communication unit, and the like.

According to some embodiments, further provided herein are non-transitory computer readable medium storing computer program instructions for executing the simulation methods, as disclosed herein.

According to some embodiments, further provided herein are simulator kits which include computer readable instructions for executing the simulation method and an automated medical device. In some embodiments, the kits may further include a phantom which mimics a region of interest of a body of a subject.

According to some embodiments, there is provided a method for simulation of planning and executing a procedure for robotic insertion and/or steering of a medical instrument toward an internal target, the simulation method includes:

- displaying a plurality of medical procedure options;
- receiving user input associated with a selected medical procedure;
- displaying one or more images of a region of interest associated with the selected medical procedure;
- receiving user input associated with a location of at least one of a target and an entry point on the one or more images;
- displaying on the one or more images a trajectory from the entry point to the target;
- receiving user input associated with advancement of the medical instrument according to the trajectory; and
- displaying on the one or more images advancement of the medical instrument according to the trajectory, the advancement simulating a medical instrument being inserted and/or steered by a robotic medical device.

According to some embodiments, the simulation method includes determining if the received user input associated with the location of the at least one of the target and the entry point is valid and/or optimal.

According to some embodiments, if it determined that the received user input associated with the location of the at least one of the target and the entry point is invalid and/or not optimal, the simulation method includes displaying on the one or more images a valid and/or optimal location of the at least one of the target and the entry point.

According to some embodiments, the simulation method includes receiving user input associated with locations of one or more obstacles between the entry point and the target.

According to some embodiments, the simulation method includes determining if the received user input associated with the locations of the one or more obstacles is valid and/or optimal.

According to some embodiments, if it determined that the received user input associated with the locations of the one or more obstacles is invalid and/or not optimal, the method includes displaying on the one or more images valid and/or optimal locations of the one or more obstacles.

According to some embodiments, the simulation method includes identifying one or more obstacles between the entry point and the target and prompting the user to confirm and/or change the identified one or more obstacles.

According to some embodiments, the simulation method includes receiving user input associated with a type of medical instrument for use in the simulation.

According to some embodiments, the simulation method includes determining if the received user input associated with the type of medical instrument for use in the simulation is optimal.

According to some embodiments, if it determined that the received user input associated with the type of medical instrument for use in the simulation is not optimal, the simulation method includes recommending to the user an optimal type of medical instrument for use in the simulation.

According to some embodiments, the simulation method includes receiving user input associated with locations of one or more checkpoints along the trajectory.

According to some embodiments, the simulation method includes determining if the received user input associated with the locations of the one or more checkpoints is valid and/or optimal.

According to some embodiments, if it determined that the received user input associated with the locations of the one or more checkpoints is invalid and/or not optimal, the simulation method includes displaying on the one or more images valid and/or optimal locations of the one or more checkpoints.

According to some embodiments, displaying the trajectory and/or displaying the advancement of the medical instrument includes:

- applying at least one of the selected medical procedure, the target, the entry point, the one or more obstacles, the trajectory, and the one or more checkpoints to a data-analysis algorithm configured to output data associated therewith;
- obtaining the output of the data-analysis algorithm; and
- generating a display based, at least in part, on the obtained output.

According to some embodiments, the simulation method includes prompting the user to confirm the displayed trajectory.

According to some embodiments, the simulation method includes calculating the trajectory in real-time.

According to some embodiments, the simulation method includes prompting the user to initiate the advancement of the medical instrument.

According to some embodiments, the simulation method includes comprising marking one or more checkpoints along the planned trajectory. According to some embodiments, the simulation method includes prompting the user to confirm and/or change the marked one or more checkpoints.

According to some embodiments, the simulation method includes issuing notifications to assist and/or guide the user during the simulation.

According to some embodiments, the simulation method includes prompting the user to choose one or more parameters associated with a virtual subject undergoing the simulated procedure.

According to some embodiments, the simulation method includes prompting the user to initiate imaging of the region of interest.

According to some embodiments, the simulation method includes displaying respiratory activity of a virtual subject.

According to some embodiments, the simulation method includes prompting the user to synchronize one or more of initiating imaging and initiating the advancement of the medical instrument with a point or a phase of a respiratory cycle of the virtual subject.

According to some embodiments, the simulation method includes displaying movement of the target during the simulation. According to some embodiments, the movement of the target is simulated using one or more data-analysis algorithms (e.g., ML/DL models).

According to some embodiments, the simulation method includes receiving user input associated with updating the trajectory.

According to some embodiments, the simulation method includes displaying an updated trajectory on the one or more images. According to some embodiments, the updated trajectory is calculated in real-time.

According to some embodiments, the simulation method includes displaying the medical instrument advancement according to the trajectory until the target is reached.

According to some embodiments, the simulation method includes determining if the target has been reached by the medical instrument.

According to some embodiments, the simulation method includes presenting to the user one or more limitations of the robotic medical device to consider during the simulation.

According to some embodiments, the robotic medical device is configured to steer the medical instrument toward the target in a non-linear trajectory.

According to some embodiments, the simulation method includes assessing a level of success of the simulation.

According to some embodiments, the simulation method includes updating a database with data associated with a completed simulation.

According to some embodiments, the simulation method includes receiving user input associated with a specified user account.

According to some embodiments, the simulation method includes saving data associated with the simulation. According to some embodiments, the saved data includes one or more tags associated with the specified user account.

According to some embodiments, the simulation method includes saving data associated with the simulation. According to some embodiments, the saved data is stored within the specified user account.

According to some embodiments, the simulation method includes assessing a level of success of the simulation and comparing the assessed level with one or more other assessed levels of similar simulations logged and/or associated with the specified user account.

According to some embodiments, the simulation method includes calculating statistics associated with the specified user account and/or a group of user accounts.

According to some embodiments, the simulation method includes analyzing the logged simulations of the specified user account and/or a group of user accounts.

According to some embodiments, the simulation method includes prompting the user to adjust one or more of: a target, an entry point, one or more obstacles, a number of checkpoints and a position of a checkpoint based, at least in part, on analyzed data associated with logged procedures of the specified user account and/or a group of user accounts.

According to some embodiments, the simulation method includes displaying animation segments during the simulation. According to some embodiments, the animation segments visualize one or more of the planning of the simulated procedure and the execution of the simulated procedure.

According to some embodiments, the animation segments include virtual reality and/or augmented reality and/or mixed reality.

According to some embodiments, the simulation method includes simulating one or more symptoms indicative of at least one of development and occurrence of a clinical complication. According to some embodiments, the clinical complication is pneumothorax. According to some embodiments, the clinical complication is internal bleeding.

According to some embodiments, the simulation method includes presenting to the user one or more error messages during the simulation.

According to some embodiments, there is provided a simulator (or—simulation system), including:

- a processor configured to execute the simulation method as disclosed herein; and
- a memory module configured to store data associated with the plurality of medical procedure options.

According to some embodiments, the simulator includes a notification device configured to generate notifications and/or alerts to the user in connection with the simulation.

According to some embodiments, the simulator includes a medical instrument module which includes an algorithm configured to operate a medical instrument.

According to some embodiments, the simulator includes a display configured to display at least the one or more images.

According to some embodiments, the simulator includes a user interface module configured to receive input from the user.

According to some embodiments, there is provided a kit for simulation of planning and executing a procedure for robotic insertion and/or steering of a medical instrument toward an internal target, the kit includes the simulator as disclosed herein, and a robotic medical device configured for inserting and/or steering the medical instrument toward the internal target.

According to some embodiments, the simulation kit includes a phantom device mimicking a region of interest in a body of a subject.

According to some embodiments, the processor of the simulation kit's simulator is configured to provide the user instructions associated with positioning and/or adjusting the positioning of the robotic medical device relative to the phantom.

According to some embodiments, the simulation kit includes a medical instrument.

According to some embodiments, there is provided a non-transitory computer readable medium storing computer program instructions for executing the simulation method disclosed herein.

According to some embodiments, there is provided a method for simulation of planning and executing a procedure for robotic insertion and/or steering of a medical instrument toward an internal target, the simulation method includes:

- displaying a plurality of medical procedure options;
- receiving user input associated with a selected medical procedure;
- displaying one or more images of a region of interest associated with the selected medical procedure;
- receiving user input associated with a location of at least one of a target and an entry point on the one or more images;
- calculating a trajectory from the entry point to the target; and simulating on the one or more images insertion and/or steering of the medical instrument by a robotic medical device, according to the calculated trajectory.

According to some embodiments, the simulation method includes presenting to the user one or more first parameters relating to selection of an optimal location for the at least one of the target and the entry point.

According to some embodiments, the simulation method includes receiving user input associated with locations of one or more obstacles between the entry point and the target.

According to some embodiments, the simulation method includes presenting to the user one or more second parameters relating to marking of optimal locations of the one or more obstacles.

According to some embodiments, the simulation method includes receiving user input associated with a type of medical instrument for use in the simulation.

According to some embodiments, the simulation method includes presenting to the user one or more third parameters relating to selection of an optimal type of medical instrument for use in the simulation.

According to some embodiments, the simulation method includes receiving user input associated with locations of one or more checkpoints along the trajectory.

According to some embodiments, the simulation method includes presenting to the user one or more fourth parameters relating to optimal locations of the one or more checkpoints along the trajectory.

According to some embodiments, the simulation method includes issuing notifications to assist and/or guide the user during the simulation.

According to some embodiments, the simulation method includes simulating movement of the target. According to some embodiments, the movement of the target is simulated using one or more data-analysis algorithms (e.g., ML/DL models). According to some embodiments, the movement of the target is simulated in real-time.

According to some embodiments, the simulation method includes receiving user input associated with updating the trajectory. According to some embodiments, the simulation method includes displaying an updated trajectory on the one or more images. According to some embodiments, the updated trajectory is calculated in real-time.

According to some embodiments, the simulation method includes simulating the insertion and/or steering of the medical instrument by the robotic medical device, according to the updated trajectory.

According to some embodiments, the simulation method includes simulating one or more symptoms indicative of at least one of development and occurrence of a clinical complication.

According to some embodiments, the simulation method includes presenting to the user one or more limitations of the robotic medical device to consider during the simulation.

According to some embodiments, the simulation method includes presenting to the user one or more error messages during the simulation.

According to some embodiments, the simulation method includes assessing a level of success of the simulation.

According to some embodiments, there is provided a method for training a user on planning and executing a procedure for robotic insertion and/or steering of a medical instrument toward an internal target, the training method includes:

displaying one or more images of a region of interest associated with the selected medical procedure;

training the user on how to optimally determine locations of at least one of a target, an entry point and one or more "no-fly" zones between the entry point and the target, the training includes at least presenting to the user one or more parameters associated with the determination;

calculating a trajectory from the entry point to the target; and simulating on the one or more images insertion and/or steering of the medical instrument by a robotic medical device, according to the calculated trajectory.

According to some embodiments, the training method includes training the user on how to optimally determine locations of one or more checkpoints along the trajectory. According to some embodiments, the training includes at least presenting to the user one or more parameters associated with (e.g., affecting or affected by) the locations of the one or more checkpoints along the trajectory.

According to some embodiments, the training method includes simulating movement of the target during a simulation/training session. According to some embodiments, the movement of the target is simulated in real-time using one or more data-analysis algorithms (e.g., ML/DL models).

According to some embodiments, there is provided a simulator (or—simulation system), including a processor configured to execute any of the methods disclosed herein, and a memory module configured to store data associated with the plurality of medical procedure options.

According to some embodiments, the simulator includes a notification device configured to generate notifications and/or alerts to the user in connection with the simulation.

According to some embodiments, the simulator includes a medical instrument module which includes an algorithm configured to operate a medical instrument.

According to some embodiments, the simulator includes a display configured to display at least the one or more images.

According to some embodiments, the simulator includes a user interface module configured to receive input from the user.

According to some embodiments, there is provided a kit for simulation of planning and executing a procedure for robotic insertion and/or steering of a medical instrument toward an internal target, the simulation kit including the simulator as disclosed herein, and a robotic medical device configured for inserting and/or steering the medical instrument toward the internal target.

According to some embodiments, the simulation kit includes a phantom device mimicking a region of interest in a body of a subject.

According to some embodiments, the processor of the simulation kit's simulator is configured to provide the user instructions associated with positioning and/or adjusting the positioning of the robotic medical device relative to the phantom.

According to some embodiments, the simulation kit includes a medical instrument.

According to some embodiments, there is provided a non-transitory computer readable medium storing computer program instructions for executing any of the methods disclosed herein.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

BRIEF DESCRIPTION OF THE DRAWINGS

Some exemplary implementations of the methods and systems of the present disclosure are described with reference to the accompanying drawings. In the drawings, like reference numbers indicate identical or substantially similar elements.

DETAILED DESCRIPTION

Figure 1:
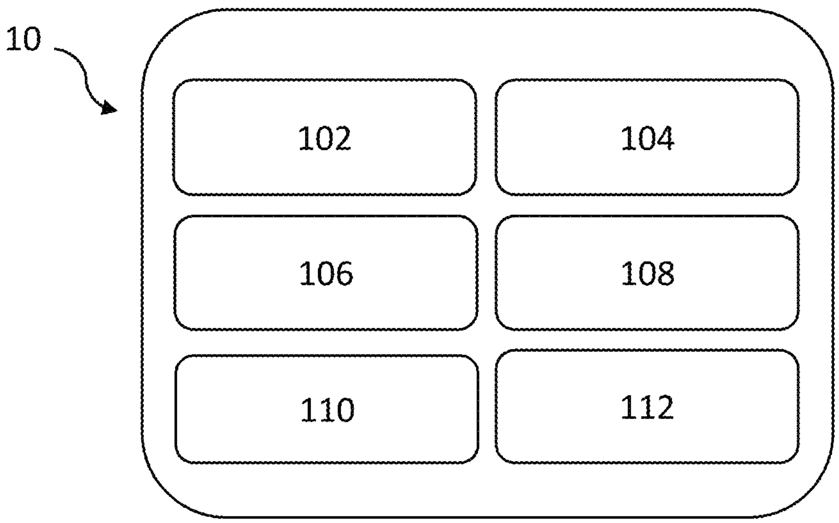
FIG. 1 shows a simplified block diagram of an exemplary simulator system for planning and executing insertion and/or steering of a medical instrument, in accordance with some embodiments of the present disclosure.

The principles, uses and implementations of the teachings herein may be better understood with reference to the accompanying description and figures. Upon perusal of the description and figures present herein, one skilled in the art will be able to implement the teachings herein without undue effort or experimentation. In the figures, same reference numerals refer to same parts throughout.

In the following description, various aspects of the invention will be described. For the purpose of explanation, specific details are set forth in order to provide a thorough understanding of the invention. However, it will also be apparent to one skilled in the art that the invention may be practiced without specific details being presented herein. Furthermore, well-known features may be omitted or simplified in order not to obscure the invention.

According to some embodiments, provided herein is system and a method for virtual simulation of at least a portion of a medical procedure of insertion and steering of a medical instrument in a body of subject, by an automated medical device. The method of the virtual simulation may include simulating one or more parts of an actual medical procedure and may include presenting, displaying and/or playing one or more images, sets of images, videos, animations of one or more portions of the medical procedure.

Reference is now made to FIG. 1, which shows a simplified block diagram of an exemplary simulator system for simulating planning and/or execution of medical instrument insertion and/or steering toward a desired target in a subject's body, in accordance with some embodiments. According to some embodiments, the simulator system 10 may include a processor/controller 102 and a display 104. In some embodiments, the simulator system 10 may include a user interface module 106, which may be in the form of one or more: buttons, switches, keys, keyboard, computer mouse, foot pedal/switch, joystick, touch-sensitive screen, virtual reality (VR) device, augmented reality (AR) device, mixed reality (MR) device, and the like. According to some embodiments, the display 104 and the user interface module 106 may be two separate components. Alternatively, they may form together a single component, for example, in case a touch-sensitive screen and/or a VR/AR/MR device is utilized. In case a VR/AR/MR device is utilized, user input may be provided, at least in part, using hand gestures. According to some embodiments, the display and/or the user interface may be components of the simulator system. According to some embodiments, the display and/or the user interface may be components of the clinical robotic system, which may be utilized during simulation sessions with the simulator. According to some embodiments, the display and/or the user interface may belong to the user or to the medical facility, such that they can be connected to the simulator system and utilized during simulation sessions.

According to some embodiments, the simulator system 10 may include a memory module 108. In some embodiments, and as described in greater detail elsewhere herein, the memory module 108 may include a database. According to some embodiments, the processor/controller 102 may be coupled to an external database, such as a database on a local server ("on premise") or on a remote server (such as, a server farm or the cloud). According to some embodiments, the memory module 108 may include a software program configured to be implemented (executed) by the processor/controller 102. According to some embodiments, the software program may include one or more algorithms for implementing the simulation of the planning and/or the insertion (according to the planning) of a medical instrument in a medical procedure. According to some embodiments, the insertion may be executed in a virtual manner by a virtual automated medical device simulating the operation of an actual automated medical device. According to some embodiments, the insertion may be executed by an actual automated medical device, using a phantom, i.e., a model of a patient's body or a specific region thereof.

According to some embodiments, the processor 102 may be used for various calculations, computing and manipulations, including, for example, but not limited to: calculation of a trajectory (such as, for example, a 2D trajectory or a 3D trajectory) for the medical instrument, updating the trajectory in real-time (i.e., during the simulation session), image processing, constructing a medical procedure scenario (optionally based, at least in part, on input received from the user), and the like. According to some embodiments, the processor may be implemented in the form of a computer (such as a PC, a laptop, a tablet, a smartphone or any other processor-based device). According to some embodiments, the processor may be configured to perform one or more of:

determine (plan) the path for a medical instrument to reach the target based on the procedure parameters (such as, for example, type of procedure, body region, target characteristics (e.g., type, shape, dimensions), target location, entry point location, type of medical instrument, obstacles (e.g., bones, blood vessels, etc.) between the entry point and the target, secondary target points, and the like); update the trajectory during the simulation (if needed, for example due to predetermined or real-time simulated target movement); present the planned and/or updated trajectory on the monitor; control the movement (insertion and/or steering) of the medical instrument (e.g., a virtual medical instrument) based on the planned and/or updated trajectory; present or determine the real-time location of the medical instrument; receive, process and visualize on the display images obtained from the memory module or in real-time from an imaging system; receive input from a user; provide output to the user, and the like, or any combination thereof.

In some embodiments, the simulation session is of a medical procedure which is operative in conjunction with an imaging system, including, but not limited to: X-ray fluoroscopy, CT, cone beam CT, CT fluoroscopy, MRI, ultrasound, or any other suitable imaging modality, and the simulated procedures may be performed with images obtained from or generated by such systems.

According to some embodiments, the simulator system 10 may comprise a medical instrument module 110. According to some embodiments, the medical instrument module 110 may include an algorithm configured to operate a virtual medical instrument. According to some embodiments, the medical instrument module 110 may include a connection mechanism configured to couple to a medical instrument, e.g., for example, in a procedure room. According to some embodiments, the medical instrument module 110 may include a coupling mechanism configured to couple to a virtual medical instrument. For example, in some embodiments, the medical instrument module 110 may include a wireless connection mechanism, such as, for example, Wi-Fi or Bluetooth, cellular network (e.g., 4G or 5G) or a wired connection (e.g., LAN, Ethernet, etc.) configured to couple to a virtual medical instrument (such as, for example, a virtual medical instrument algorithm stored onto a cloud) and/or a tangible medical instrument.

According to some embodiments, the simulator system 10 may comprise a notification device 112 (also referred to as "alert device"). The notification device 112 may be in communication with one or more of the processor/controller 102, the display 104, the user interface module 106 and the memory module 108. According to some embodiments, the notification device 112 may be configured to receive input, such as confirmation or rejection, from the user via the user interface module 106. According to some embodiments, the notification device 112 may be used to assist the user during the planning of the virtual procedure and/or during the advancement of the medical instrument (virtual and/or tangible) according to the planning, by generating and/or presenting assisting instructions and/or explanations of the different steps of the simulation process. According to some embodiments, the alerts/notifications may include visual instructions, such as, for example, displaying captions or written instructions and/or explanations on the display 104 or, specifically, on the image-view/s. According to some embodiments, the alerts/notifications may include audio alert/instructions, such as, for example, voice instructions. According to some embodiments, the notification device 112 may comprise an audio transmitting device, such as speakers.

Figure 2A:
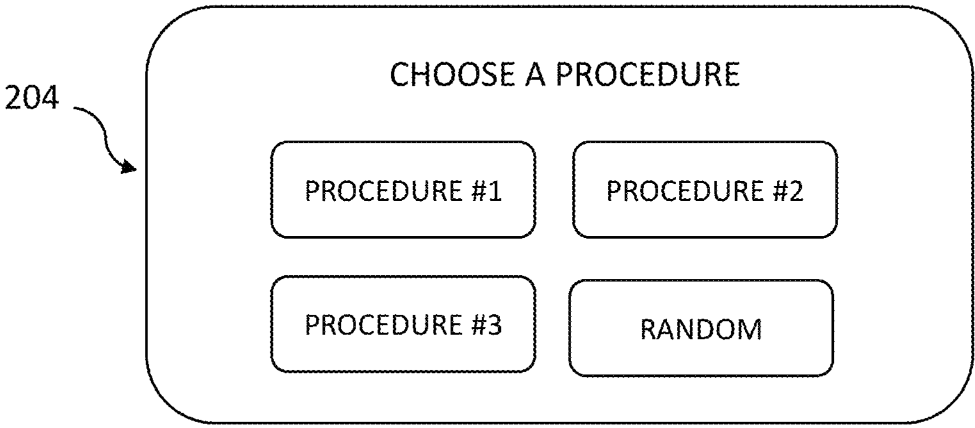
FIGS. 2A-2B show exemplary selection screens displayed to a user and present a plurality of procedure options (FIG. 2A) and a plurality of case options (FIG. 2B), in accordance with some embodiments of the present disclosure.
Figure 2B:
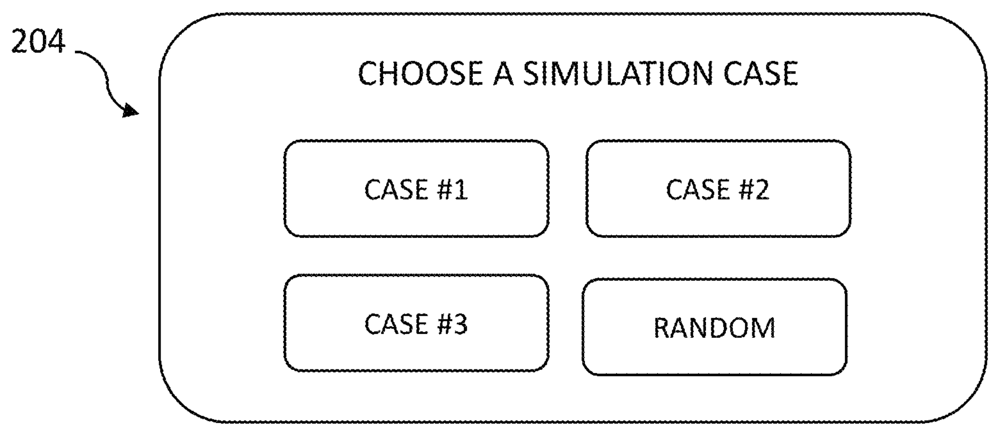

Reference is now made to FIGS. 2A-2B, which show exemplary selection screens which may be presented to the user on a display 204, for example the display of simulator system 10 shown in FIG. 1. As shown in FIG. 2A a plurality of procedure options may be displayed on display 204 for the user to choose from, shown in FIG. 2A as "PROCEDURE #1", "PROCEDURE #2" and "PROCEDURE #3". The procedure option may pertain to one or more of different procedure types, different target organs, etc. According to some embodiments, a "RANDOM" option may additionally be presented to the user. The "RANDOM" option may pertain to a random procedure being selected by a processor, for example processor 102 of simulator system 10 shown in FIG. 1. According to some embodiments, the random procedure may be randomly selected by the processor, for example from a plurality of procedures stored in a memory module, for example memory module 108 of simulator system 10 shown in FIG. 1. Advantageously, a "RANDOM" (or "shuffle") option allows the user to practice/train on a variety of procedures without resorting to a specific procedure type or specific target organ, thereby allowing the user to train and gain experience in a larger scope of versatile medical procedures. According to some embodiments, displaying a plurality of procedure options may include presenting a plurality of categories (such as, for example, a plurality of selectable options), configured to allow a user to select one or more categories. According to some embodiments, the plurality of categories may include procedure types (for example, biopsy, ablation, fluid drainage, drug delivery, etc.) and/or target organ options (e.g., liver, lung, breast, spine, etc.). Additionally, according to some embodiments, once the user selects a category, such as a specific target organ, the method may further include presenting to the user a plurality of sub-categories within the selected category. The sub-categories may be, for example, different simulation cases, shown in FIG. 2B as "CASE #1", "CASE #2" and "CASE #3". The different cases may differ from each other in one or more of the following characteristics: patient type (such as, for example, body type, anatomy, age, gender, etc.), patient position (such as, for example, prone, supine, etc.), target characteristics (such as, type, shape, size, condition, etc.), expertise level (difficulty level of the procedure, target location which is difficult to reach, etc.), type of imaging modality, and the like. According to some embodiments, each of the above characteristics (i.e., patient type, patient position, etc.) may each be a sub-category which is presented to the user to choose one option from. According to some embodiments, the user can select from only one sub-category in a single simulation session. According to some embodiments, the user can select from multiple sub-categories during a single simulation session, so as to create a "tailor-made" case for him/her to practice on. According to some embodiments, a "RANDOM" option may additionally be presented to the user, such that if chosen, the processor will randomly select the case or combination of characteristics for the simulation session. According to some embodiments, the one or more sub-categories may be presented in the form of different scans and/or image-views. According to some embodiments, the displayed options (such as procedures, categories, and/or sub-categories) may be displayed in the form of one or more of image-views (e.g., scans), descriptions, titles, and the like, or any combination thereof. According to some embodiments, once an option is selected (e.g., a procedure, category and/or sub-category), one or more scans and/or image-views associated with the selected option are displayed.

According to some embodiments, the procedure options may include a list of medical procedures. According to some embodiments, the procedure options may include a list of regions of interest (or target organs). According to some embodiments, the procedure options may include a list of clinical interventional procedures, such as a biopsy, ablation, and the like. According to some embodiments, the regions of interest may include any one or more of a target organ, a target type (e.g., tumor, lesion, abscess, etc.), and the like. According to some embodiments, the plurality of medical procedures may be categorized by any one or more of: type of procedure, organ and/or tissue type, type of medical instrument (e.g., introducer, needle, ablation probe, etc.), type of medical complication, patient history, patient's medical risks, type of imaging modality and/or medical specialty of the procedure.

According to some embodiments, the procedure options may be obtained from a memory module, for example memory module 108 of simulator system 10 shown in FIG. 1. According to some embodiments, and as described in greater detail elsewhere herein, the procedure options may be updatable over time within the memory module.

According to some embodiments, the user may be required/prompted to provide input regarding a selected procedure. According to some embodiments, the input is received by the processor via a user interface module, for example user interface module 106 of the simulator system 10 shown in FIG. 1. According to some embodiments, the input may include any one or more of a selected procedure type, a selected region of interest, and a selected random option associated with a random procedure type and/or a random region of interest. According to some embodiments, and as described in greater detail elsewhere herein, the input may include data associated with any one or more of a user profile, a username, an organization, a training program, a score relating to a previous procedure, a specialty training program, and the like, or any combination thereof.

Figure 3:
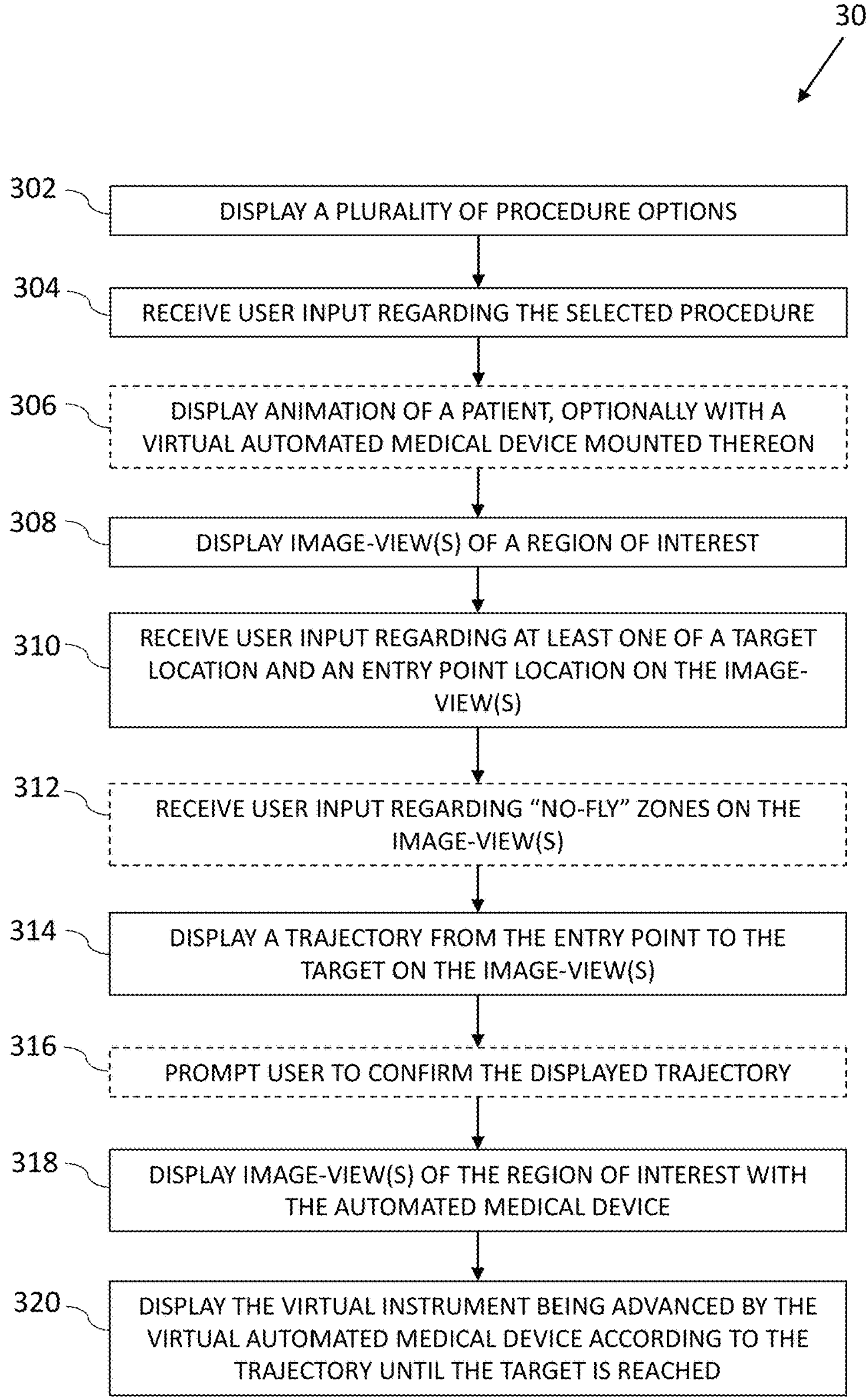
FIG. 3 shows a flowchart showing steps in an exemplary method for simulation of planning and executing robotic insertion and/or steering of a medical instrument toward an internal target, in accordance with some embodiments of the present disclosure.

Reference is now made to FIG. 3, which shows a flowchart of steps in an exemplary method for simulation of a medical procedure in which a medical instrument is inserted and/or steered toward a target, in accordance with some embodiments. According to some embodiments, one or more of the steps shown in FIG. 3 may be optional and one or more of the steps may be repeated.

According to some embodiments, the method 30 is for simulation of planning and executing insertion/steering of a medical tool using an automated medical device, such as the automated medical device disclosed in co-owned U.S. Patent Application Publication No. 2019/290,372, which is incorporated herein by reference in its entirety. According to some embodiments, the method 30 may be implemented to train or teach a user to operate the automated medical device to allow the insertion and/or steering of a medical instrument from an entry point to a desired target. According to some embodiments, operating the automated medical device may include planning, using a dedicated software application, a trajectory for the medical instrument from an entry point to a desired target, and inserting/steering the medical instrument toward/into the target based on the planned trajectory and/or an updated trajectory, as will be described hereinafter, using the automated medical device. The planning and executing of the procedure may be based on methods and algorithms described, for example, in U.S. Pat. Nos. 8,348,861, 8,663,130 and/or co-owned International Patent Application Publication No. WO 2021/105,992, all of which are incorporated herein by reference in their entireties. As shown in FIG. 3, method 30 includes, at step 302, presenting to a user a plurality of procedure options. For example, the user may be prompted to select a procedure type (e.g., biopsy, ablation, fluid drainage, drug delivery, etc.) and/or a target organ (e.g., lung, liver, kidney, spine, para-aortic lymph node, retroperitoneal lymph node, etc.). In some embodiments, the user may be additionally prompted to select a specific simulation case. Selection of a procedure type, target organ and/or simulation case may be referred to hereinafter collectively as selection of "a procedure". Next, at step 304, user input regarding the selected procedure is received.

At optional step 306, an animation of a patient on a patient bed in the procedure room may be displayed. In some embodiments, the patient may be displayed in the animation already having an automated (robotic) medical device mounted thereon, or in close proximity, thereto.

According to some embodiments, an animation of a patient lying on the patient bed may be displayed prior to procedure selection, and an animation of the patient with a robot positioned on the patient's body, or in close proximity thereto, may be associated with the selected procedure, corresponding to the relevant region of interest, and displayed following the user selecting a procedure. According to some embodiments, the animation may be displayed to the user after a planned trajectory for the simulated procedure has been displayed. According to some embodiments, the animation may be based, at least in part, on data stored in a memory module, for example memory module 108. According to some embodiments, the animation may include one or more images generated by algorithm(s), wherein the algorithm(s) may be stored on the memory module. According to some embodiments, the algorithm is configured to receive data associated with the selected procedure and/or planned trajectory. According to some embodiments, the algorithm is configured to generate one or more images and/or animations in which the selected procedure and/or region of interest is produced. According to some embodiments, the method may include generating, using the algorithm(s), an animation in which the selected procedure is produced. According to some embodiments, the animation may include a 2D animated video or presentation or a 3D animated video or presentation. According to some embodiments, the animation may be in the form of a virtual reality and/or augmented reality and/or mixed reality experience.

According to some embodiments, the preparation of the automated device and its related components for the procedure may also be displayed to the user, either by means of animation segments or by means of video segments of actual preparations. Such preparations may include, for example, draping of the automated device, preparation of an insertion module which holds the medical instrument, such as the insertion module disclosed in co-owned U.S. Pat. No. 11,083,488, which is incorporated herein by reference in its entirety, connection of the insertion module to the automated device, etc. According to some embodiments, the simulation may include the user executing the procedure preparations, in whole or in part (i.e., executing only one or more of the actions which are part of the preparation for a procedure) using a tangible device (a functional device or a model thereof) and/or components and/or accessories thereof.

According to some embodiments, following the selection of the simulated procedure, the simulation method may incorporate the actual clinical software application of the automated system which is used by users (e.g., physicians) during clinical procedures. Alternatively, a dedicated software application resembling the clinical software application may be used. According to some embodiments, the user may be required to provide input associated with a type of medical instrument (virtual or tangible) to use in the simulation. According to some embodiments, a plurality of medical instrument options may be displayed for the user to select therefrom. The medical instrument options may include different instrument types (e.g., introducer, needle, ablation probe, etc.), different instrument dimensions (e.g., gauge, length, etc.), different instrument brands/manufacturers, or a combination thereof. According to some embodiments, the plurality of medical instrument options may be based, at least in part, on data stored on the memory module. According to some embodiments, the memory module may include a database of medical instruments. According to some embodiments, the database may be updated using software (for example, from a local or remote server or a cloud) and/or manually such as, for example, by a user.

At step 308, an image or a set of images of the relevant region of interest is presented, for example utilizing the Graphical User Interface (GUI) of the clinical SW application or the GUI of the dedicated SW application. According to some embodiments, the images may include one or more images obtained from an imaging system and/or the like. According to some embodiments, the images may include images stored in the memory module and/or images obtained from a local or remote server (e.g., a cloud server). According to some embodiments, the images may be obtained from the imaging system in real-time, i.e., during the simulation session. According to some embodiments, the images may include DICOM images. According to some embodiments, the DICOM images may be obtained from actual previously executed medical procedures or they may be general (empty) images of a region of interest. As used herein, DICOM (Digital Imaging and Communications in Medicine) is the standard for the communication and management of medical imaging information and related data. The DICOM images may display data produced by a wide variety of imaging device types, including, CT, cone beam CT, CT fluoroscopy, MRI, ultrasound, X-ray, fluoroscopy, endoscopy, etc. According to some embodiments, the simulation method may enable the user to choose which image-view/s he/she would like to be displayed, from a plurality of different image-views generated from a set of images (or "image-frames" or "slices"). Such image-views may be, for example, image-views pertaining to different planes or orientations (e.g., axial, sagittal, coronal, pseudo axial, pseudo sagittal, pseudo coronal, etc.) or additionally generated views (e.g., trajectory view, tool view, 3D view, etc.). In some embodiments, the user may be prompted to initiate imaging (e.g., a planning scan) following which the images will be presented to the user. In some embodiments, the user initiating imaging includes the user selecting a corresponding action on the display. In some embodiments, initiating imaging includes the user providing corresponding voice commands. In some embodiments, the user may be prompted to select a scan volume.

Next, at step 310, the user may be prompted to mark at least one of a target and an entry point on the image-view. According to some embodiments, the method may include the processor automatically marking the target on the image-view. According to some embodiments, the method may include identifying and calculating the position of the target using an algorithm stored onto the memory module or a local or remote server. According to some embodiments, the method includes marking the target location based, at least in part, on data stored in the memory module. According to some embodiments, the method may include the processor marking several selectable optional entry points for the user to choose from. The optional entry points may be suggested by the processor based on the marked target and using image processing methods and/or using data-based algorithms (e.g., AI models) based on data collected in previous actual procedures, as well as, optionally, data obtained from previous successful simulation sessions. According to some embodiments, the method may include the processor marking a single (optimal) entry point on the image. According to some embodiments, the method may include calculating, using an algorithm, one or more or optional entry points and/or optimal entry points. According to some embodiments, the method includes marking one or more optional and/or optimal entry points based, at least in part, on stored data. According to some embodiments, marking one or more optional and/or optimal entry points may be accompanied by an explanation displayed (visually and/or audibly) to the user as to the considerations relating to the marking of the one or more optional and/or optimal entry points, such as target location, obstacle/s en route, associated entry angle, robotic device limitations (e.g., workspace limitations, registration constraints, etc.), medical instrument characteristics (e.g., length, gauge, etc.).

At optional step 312 the user may be prompted to mark on the image-view "no-fly" zones (or—obstacles), i.e., regions which should be avoided by the medical tool, as they include bones, blood vessels, etc., as described in further detail elsewhere herein.

At step 314, a planned trajectory from the entry point to the target is displayed on the image(s). According to some embodiments, the displayed trajectory may be retrieved from the memory module of the simulator or from a local or remote server. According to some embodiments, the displayed trajectory may be a pre-determined trajectory. According to some embodiments, the displayed trajectory may be a trajectory planned during a previous clinical procedure or during a previous simulation session pertaining to the same selected procedure. According to some embodiments, the user may be prompted to initiate calculation of the trajectory. According to some embodiments, the calculation of the trajectory may be executed in real-time. As further detailed below, the trajectory may be calculated based on various parameters, including for example, but not limited to: entry point, target, obstacles, body region, type of medical instrument, type of medical procedure, and the like. According to some embodiments, the planned trajectory is a 2D trajectory. According to some embodiments, the planned trajectory is a 3D trajectory. According to some embodiments, the planned trajectory is a linear trajectory. According to some embodiments, the planned trajectory is a non-linear trajectory. At optional step 316 the user may be prompted to confirm the displayed trajectory.

At step 318, image(s) of the region of interest showing the automated device mounted on the patient or positioned in close proximity thereto may be displayed. According to some embodiments, the user may be prompted to initiate imaging (e.g., a registration scan), following which the image(s) will be presented. According to some embodiments, the images may be stored images. According to some embodiments, the images may be obtained from an imaging system in real-time. According to some embodiments, an animation or a video of the automated device being attached to the patient or positioned in proximity thereto may be displayed in addition to displaying the image(s) on the GUI. According to some embodiments, the automated device may be a body-mountable device, which may be attached to the subject's body either directly or by means of a mounting apparatus, such as the mounting base disclosed in co-owned U.S. Pat. No. 11,103,277, or the attachment frame disclosed in co-owned U.S. Patent Application Publication No. 2021/228,311, both of which are incorporated herein by reference in their entireties. In such embodiments, the displayed animation may be of a virtual automated medical device being mounted on virtual patient's body. In other embodiments, the automated device may be configured for coupling/attaching to a dedicated arm (stationary, robotic or semi-robotic) or base which is secured to the patient's bed, to a cart positioned adjacent the patient's bed or to the imaging device, and held on the patient's body or in close proximity thereto, as described, for example, in U.S. Pat. Nos. 10,507,067 and 10,639,107, both of which are incorporated herein by reference in their entireties. The position of the virtual automated device on (or in proximity to) the virtual patient's body may correspond to the location of the target organ. According to some embodiments, the simulation may be executed, at least in part, using an automated device (real or model thereof) and an imaging device, together with a phantom device. In such embodiments, the user is able to practice "hands-on" the coupling of the automated device to the patient, either directly or using a mounting apparatus, or to a dedicated arm. According to some embodiments, the method may include training the user on how to properly position the medical device on the patient's body (or in close proximity thereto), by simulating the device's position and orientation relative to the body on the images, using a virtual device, and providing instructions regarding required corrections to the actual (physical) positioning of the device (or model) relative to the phantom, as disclosed, for example, in co-owned International Patent Application Publication No. WO 2021/111,445, which is incorporated herein by reference in its entirety. The simulated position and orientation suggested by the simulator's processor may be based on the displayed images and the calculated trajectory and/or on data obtained from previous similar procedures using algorithm(s), such as machine learning and/or deep learning algorithm(s), for example. According to some embodiments, the position and orientation recommendation may be based, inter alia, on one or more of the following parameters: scanning/registration limitations (such as, maximal angles), device workspace limitations, patient characteristics (such as, body shape, body contour), etc.

At step 320, the advancement of the medical instrument according to the trajectory, is displayed on the image-view(s), and optionally also in the form of animation, videos, series of images, and the like. According to some embodiments, the advancement of the medical instrument may be displayed until the target is reached.

Figure 4:
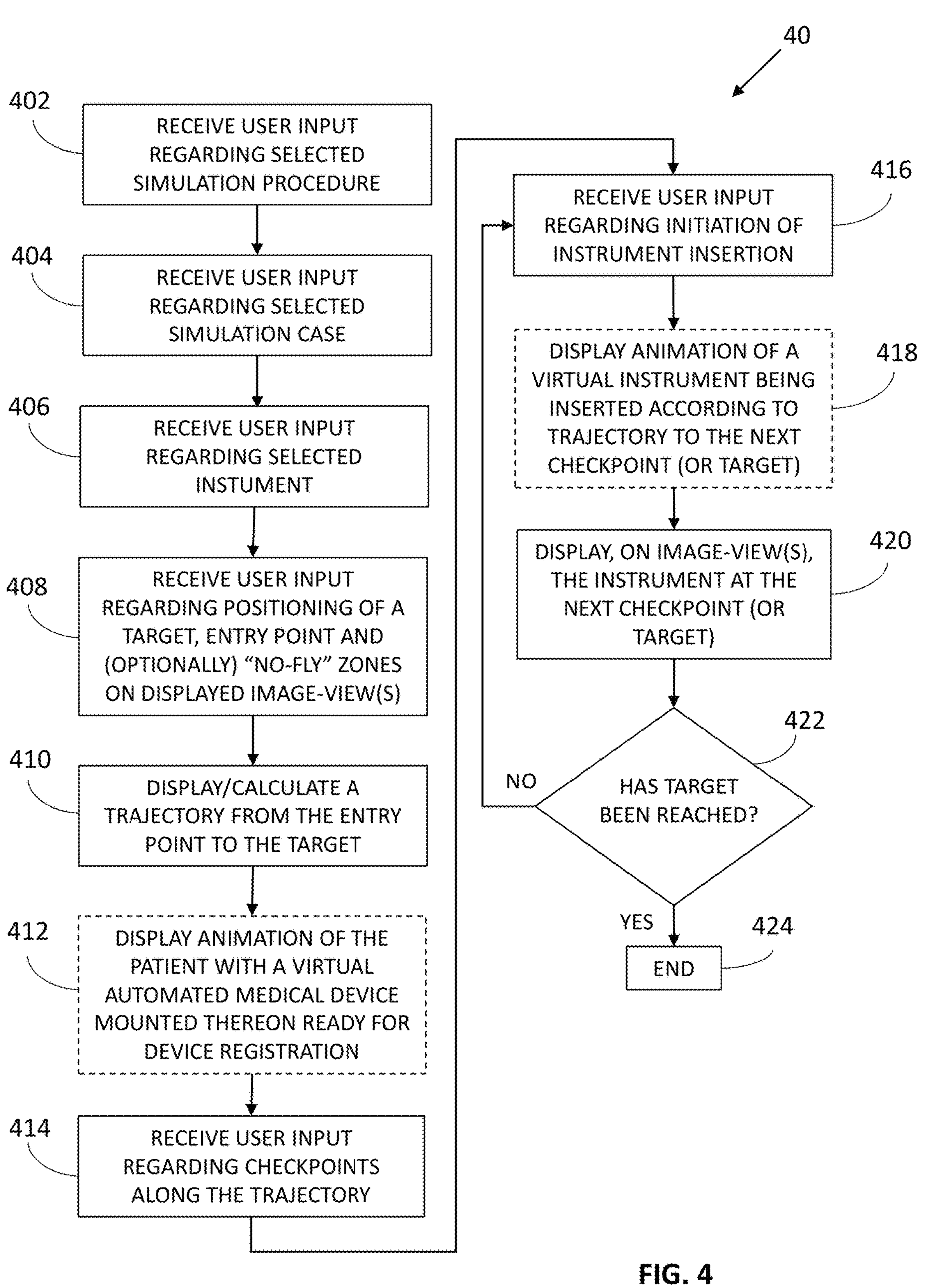
FIG. 4 shows a flowchart showing steps in another exemplary method for simulation of planning and executing robotic insertion and/or steering of a medical instrument toward an internal target, in accordance with some embodiments of the present disclosure.

Reference is now made to FIG. 4, which shows a flowchart of steps in another exemplary method for simulation of a procedure for planning and executing robotic insertion and/or steering of a medical instrument toward a target in the body of a patient, in accordance with some embodiments. According to some embodiments, one or more of the steps shown in FIG. 4 may be optional and one or more of the steps may be repeated. According to some embodiments, method 40 may include one or more steps associated with method 30. According to some embodiments, a plurality of procedure options are displayed on the monitor for the user to choose from, and at step 402, the method includes receiving user input regarding a selected procedure. According to some embodiments, prior to displaying the procedure options, or after receiving user input regarding a selected procedure, the method may include displaying an animation of a virtual procedure room with a patient lying on a patient bed. According to some embodiments, a plurality of case options relating to the selected procedure may be displayed on the monitor, for the user to choose from. For example, several stored image-views collected from different procedures belonging to the same procedure category (e.g., procedure type or target organ) may be displayed on the monitor for the user to choose from. According to some embodiments, the user may be prompted to select one of the presented case options, and at step 404, the method includes receiving user input regarding a selected simulation case.

According to some embodiments, at step 406, the method may include receiving user input regarding the selected instrument for the procedure. According to some embodiments, a plurality of medical instrument options may be displayed for the user to select therefrom. The medical instrument options may include different instrument types (e.g., introducer, needle, ablation probe, etc.), different instrument dimensions (e.g., gauge, diameter, length, etc.), different instrument brands/manufacturers, or a combination thereof. According to some embodiments, the plurality of presented medical instrument options may be based, at least in part, on a database of medical instruments stored on the memory module or on a local or remote server. According to some embodiments, the method may include presenting to the user, e.g., via the display and/or via speakers, limitations and/or advantages associated with the different instruments, to assist the user in selecting the appropriate/optimal instrument for the simulated procedure. Exemplary limitations may include, for example, instrument flexibility, which may limit trajectory adjustment during the simulated procedure, should it be required. For example, a thinner instrument is more flexible and may thus, under certain circumstances, be easier to steer when the target is located at a hard-to-reach region of the body or should the target move during the procedure. Such presentation of the limitations and/or advantages of associated with the different instruments may take place prior to the user selecting the instrument for the simulation, or after the user selects the instrument for the procedure, enabling the user to change his/her selection.

According to some embodiments, at step 408, the method may include receiving user input regarding positioning of a target and an entry point on the selected image-view. According to some embodiments, and as described in greater detail elsewhere herein, the simulation system (e.g., the memory module thereof) may include one or more algorithms configured to calculate one or more of the target location and/or optional/optimal entry point(s). According to some embodiments, the algorithms may include ML/DL models configured to identify the target and/or identify optional/optimal entry point(s). According to some embodiments, the simulation method may include prompting a user to mark "no-fly" zones/obstacles on the image-view. According to some embodiments, the method may include automatically identifying and/or marking on the image-view(s) one or more potential obstacles, using image processing methods and/or algorithm(s), which may include ML/DL model(s), and prompting the user to confirm the marked obstacles or edit them. According to some embodiments, the method may include presenting an explanation (e.g., visually and/or audibly) to the user as to the considerations (e.g., limitations, constraints and/or advantages) relating to the marking of the one or more of the target, optional/optimal entry point(s) and "no-fly" zones.

According to some embodiments, at step 410, the method includes displaying or calculating a trajectory from the entry point to the target. According to some embodiments, the trajectory may be retrieved from the memory model or the local or remote server. According to some embodiments, the trajectory may be calculated in real-time. In such embodiments, the trajectory may be calculated taking into account various variables, including, but not limited to: the type of the selected medical instrument, the tissues through which the medical instrument is to be (virtually) inserted, the location of the target, the size of the target, the entry point, and the like, or any combination thereof. According to some embodiments, the method may include calculating and displaying to the user more than one trajectory; a trajectory which is based on the current user selection (e.g., relating to the selected instrument, the marked target, the marked entry point, etc.), and one or more additional trajectories, which may be preferable to the trajectory calculated based on the current user selection, and which may require different user selection. According to some embodiments, the method may include presenting to the user the parameters based on which the one or more alternative trajectories were calculated, and providing an explanation regarding the impact and/or advantages of the different parameters on the trajectory and/or the disadvantages/limitations of the current user selection. In such embodiments, the method may enable the user to edit one or more of his/her previous selections and initiate recalculation of the trajectory.

Further taken into account in determining the trajectory may be various obstacles, which may be found/identified along the path and should be avoided, to prevent damage to neighboring tissues and/or to the medical instrument in a real clinical procedure. According to some embodiments, safety margins may be marked along the trajectory, to ensure a minimal distance between the trajectory and potential obstacles en route. According to some embodiments, the width of the safety margins may be symmetrical in relation to the trajectory. According to some embodiments, the width of the safety margins may be asymmetrical in relation to the trajectory. According to other embodiments, the width of the safety margins may be determined and/or adjusted by the user. According to some embodiments, the trajectory may be two-dimensional. According to some embodiments, the trajectory may be three-dimensional. According to some embodiments, the trajectory may be calculated and displayed in two dimensions on two different planes which may be used in determining the 3D trajectory by superpositioning the two calculated 2D (planar) trajectories, that may be perpendicular, as described, for example, in abovementioned International Application Publication No. WO 2021/105,992.

According to some embodiments, the trajectory may include any type of trajectory, including linear trajectory or a non-linear trajectory having any suitable degree of curvature. The planning of the trajectory and the steering of the instrument may be based on a model of the medical instrument as a flexible beam having a plurality of virtual springs connected laterally thereto to simulate lateral forces exerted by the tissue on the instrument, calculating the trajectory through the tissue on the basis of the influence of the plurality of virtual springs on the instrument, and utilizing an inverse kinematics solution applied to the virtual springs model to calculate the required motion to be imparted to the instrument to follow the planned trajectory, as described in abovementioned U.S. Pat. No. 8,348,861.

According to some embodiments, at optional step 412, an animation of a virtual patient with a virtual automated medical device (robot) mounted thereon (or in close proximity thereto) may be displayed, optionally following, or preceding, prompting the user to initiate a registration scan.

According to some embodiments, at step 414, the method includes receiving user input regarding the positioning of checkpoints along the displayed/calculated trajectory. Checkpoints are points along the trajectory at which the advancement of the instrument is paused and imaging is initiated, to verify the location of the instrument within the patient's body, specifically in order to verify that the instrument (e.g., the tip thereof) follows the planned trajectory, and to determine the current target position, such that if the target has moved from its initial position based upon which the trajectory was determined, or from a previously confirmed position (e.g., the target's position as identified in images obtained at a previous checkpoint), recalculation (update) of the trajectory may be initiated, either automatically or manually by the user. According to some embodiments, the received user input may be associated with at least one of the number of checkpoints, the position of the checkpoints, and the distance (spacing) between two or more checkpoints or between the entry point and the first checkpoint or between the last checkpoint and the target. According to some embodiments, the method may include identifying and/or marking one or more checkpoints based, at least in part, on stored data (e.g., in the memory module). According to some embodiments, the method may include identifying and/or calculating, using one or more algorithms, one or more optimal checkpoints. The algorithm(s) may include ML/DL model(s) configured to calculate optimal checkpoint locations along the trajectory, as disclosed, for example, in co-owned International Patent Application Publication No. WO 2021/214,754, which is incorporated herein by reference in its entirety. According to some embodiments, the checkpoints may be predetermined and/or determined before and/or during the procedure simulation. According to some embodiments, the checkpoints may include spatial checkpoints (for example, regions or locations along the trajectory, including, for example, specific tissues, specific regions, length or location along the trajectory (for example, every 20-50 mm), and the like). According to some embodiments, the checkpoints may be temporal checkpoints, i.e., a checkpoint performed at designated time points during the procedure (for example, every 2-5 seconds). According to some embodiments, the checkpoints may include both spatial and temporal check points. According to some embodiments, the checkpoints may be spaced apart, including the first checkpoint from the entry point and the last checkpoint from the target, at an essentially similar distance along the trajectory. According to some embodiments, one or more default checkpoints along the trajectory may be automatically marked, and the user may then be prompted to confirm the default checkpoints or to change the number and/or the locations of the displayed checkpoints.

According to some embodiments, at step 416, the method includes receiving user input regarding initiation of instrument advancement. Initiating the insertion and/or steering procedure may simulate the user pressing an activation pedal (e.g., a foot pedal) and/or button, either from within the procedure room of from a remote location (e.g., the control room or a location external to the medical facility) using a remote control unit, in a real clinical procedure. According to some embodiments, the simulator system may include such a pedal/button which the user is required to press to initiate the advancement of the virtual (or tangible) instrument. According to some embodiments, the steering of the medical instrument is carried out in a 3D space, wherein the steering instructions are determined on each of two perpendicular two-dimensional (2D) planes, which are superpositioned to form the steering in the 3D space.

According to some embodiments, at optional step 418, the method may include displaying an animation of a virtual instrument being steered by a virtual robot to the next checkpoint or to the target. According to some embodiments, the animation may include the selected medical instrument. According to some embodiments, the animation may be stored in a memory module, for example memory module 108. According to some embodiments, the animation may be generated in real-time using algorithm(s). According to some embodiments, the animation may include a virtual medical instrument being steered by a virtual automated medical device from one checkpoint to the next along the trajectory. According to some embodiments, the method may include displaying the advancement of the instrument until target is reached. According to some embodiments, the animation of the virtual instrument being advanced may be shown on a cross-sectional view of the virtual patient, which may correspond to the image-view presented on the display.

According to some embodiments, at step 420, the method includes displaying, on the image-view, the instrument at the next checkpoint (or at the target, if the target has been reached). According to some embodiments, prior to such displaying, the user may be prompted to initiate imaging. According to some embodiments, the user initiating imaging (e.g., by clicking a button on the GUI or using a hand gesture) may result in retrieval of a stored image. According to some embodiments, the user initiating imaging may result in real-time imaging of the image of interest (e.g., when the simulation session is carried out using a robot (or a model of a robot) and a phantom). According to some embodiments, the user may be required to set the scan volume. According to some embodiments, at step 422, the method includes checking if the instrument has reached the target. If the target has been reached, the simulation ends, at step 424, whereas if the target has not yet been reached (i.e., the instrument is currently at one of the checkpoints along the trajectory), the simulation continues, with steps 416-422 being repeated until the target is reached and the simulation then ends.

According to some embodiments, the simulation method may include identifying, highlighting and/or marking on the image-view/s, during the simulation (i.e., in real-time), areas and/or points in which the medical instrument has touched and/or passed too close to a potential obstacle. According to some embodiments, the obstacles may be identified by an algorithm and/or labeled on a scan/image within the memory module or a local or remote server (e.g., cloud). According to some embodiments, the method may include updating the memory, periodically or continuously, with obstacles associated with a stored image. According to some embodiments, the method may include alerting a user of an unmarked obstacle during the simulated procedure. According to some embodiments, if the user is prompted to manually mark obstacles but he/she did not mark an obstacle identified by the processor (for example, a blood vessel located between the entry point and the target), and proceeded to initiate calculation of a trajectory, the simulator may alert the user that a potential obstacle has been overlooked and will not calculate the trajectory until all potential obstacles have been marked and/or confirmed by the user. According to some embodiments, if the user did not mark, for example, a blood vessel located en route to the target, the simulator may alert the user during the simulation of the insertion procedure, or immediately thereafter, if the medical instrument touched or passed too close to it, based on proximity calculations. According to some embodiments, the alert may include highlighting/marking the relevant obstacle on the image-view, an alert pop-up window appearing on the display, a text box, and/or an auditory alert. According to some embodiments, the method may include displaying an alert in each relevant image-view during the simulation and/or displaying the alert on the last image-view, i.e., showing the medical instrument at the target, such that if an alert was presented on more than one image-view throughout the simulation, or alerts were not previously presented to the user but the instrument touched or passed too close to one or more obstacles during the steering simulation, all the obstacles along the entire trajectory followed by the instrument will appear together on the last image-view. Displaying the alert in the image-view in which the medical instrument reached the target allows a user to complete the simulation before receiving feedback regarding any missed obstacles.

According to some embodiments, any one of displaying the trajectory planning process, displaying the planned trajectory and displaying the virtual medical instrument advancement on the image-view/s and/or animation segments may include applying at least one of the selected procedure, the planned and/or updated trajectory, one or more checkpoints, the target, and one or more obstacles to one or more algorithms (e.g., ML/DL model(s)) configured to output data associated therewith.

According to some embodiments, any one of displaying the trajectory planning process, displaying the planned trajectory and displaying the virtual medical instrument advancement on the image-view/s and/or animation segments may include obtaining the output of one or more algorithms and generating a display based, at least in part, on the obtained output. According to some embodiments, the algorithm(s) may include one or more ML/DL models. According to some embodiments, the algorithm(s) may be configured to receive at least one of the selected target, the selected entry point, the one or more selected obstacles, the one or more selected checkpoints, and the like.

According to some embodiments, any one of displaying the trajectory planning process, displaying the planned trajectory and displaying the virtual medical instrument advancement may include displaying a 2D presentation of the procedure. According to some embodiments, any one of displaying the trajectory planning process, displaying the planned trajectory and displaying the virtual medical instrument advancement may include displaying on one or more images based on, at least in part, CT scans, visual camera images, x-ray scan images, and the like, associated with actual medical procedures and/or as seen in the medical procedures in which the medical instrument is used in real operation.

According to some embodiments, the method may include alerting the user and/or issuing notifications to assist the user during the planning and/or the execution of the simulated procedure. According to some embodiments, the alerts/notifications may include instructions and/or explanations of the different steps of the simulation process. The notifications may be issued during the planning and/or execution steps and/or during the display of the animation segments. According to some embodiments, the notifications may include visual instructions, such as, for example, displaying captions or written instructions within the display, for example display 104 or, specifically, on the image-view/s. According to some embodiments, the notifications may include audio instructions, such as, for example, voice instructions. According to some embodiments, the alerts may be implemented by an alert device, for example alert device 112 of simulator system 10 shown in FIG. 1.

Figure 5:
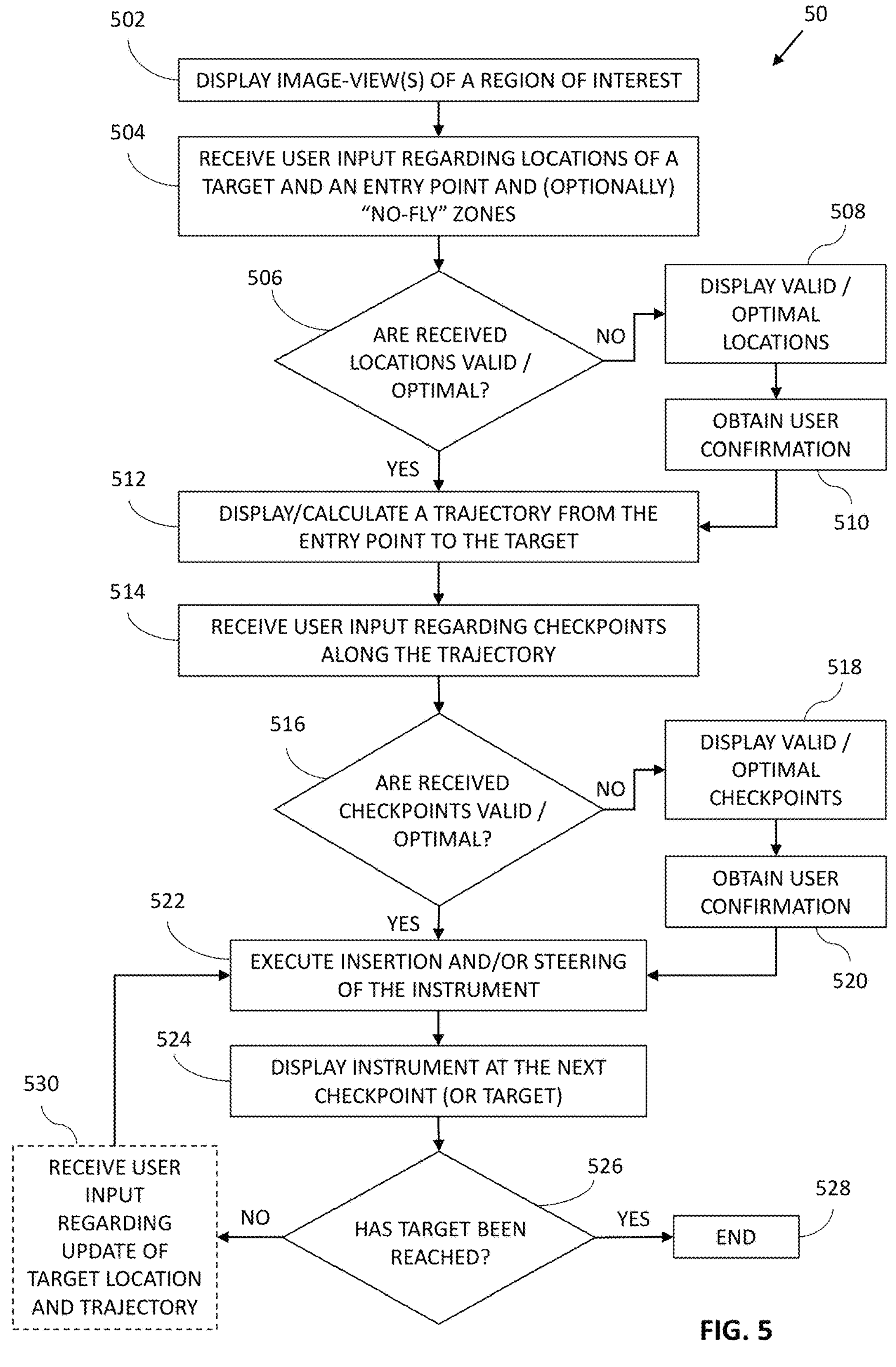
FIG. 5 shows a flowchart showing steps in another exemplary method for simulation of planning and executing robotic insertion and/or steering of a medical instrument toward an internal target, in accordance with some embodiments of the present disclosure.

Reference is now made to FIG. 5, which shows a flowchart of steps in another exemplary method for simulation of a procedure for planning and executing robotic insertion and/or steering of a medical instrument toward a target in the body of a patient, in accordance with some embodiments. According to some embodiments, one or more of the steps shown in FIG. 5 may be optional and one or more of the steps may be repeated. According to some embodiments, the steps shown in FIG. 5 may be executed after a procedure and/or case was selected for a specific simulation session.

According to some embodiments, at step 502, an image or a set of images of the relevant region of interest is presented, for example utilizing the GUI of the clinical SW application or the GUI of the dedicated SW application. According to some embodiments, the images may include one or more images obtained from an imaging system, including CT, cone beam CT, CT fluoroscopy, MRI, ultrasound, X-ray, fluoroscopy, endoscopy, etc. According to some embodiments, the images may include images stored in the memory module and/or images obtained from a local or remote server (e.g., a cloud server). According to some embodiments, the images may be obtained from actual previously executed medical procedures or they may be general (empty) images of the region of interest, according to the selected procedure/case to be simulated. According to some embodiments, prior to such displaying, the user may be required to initiate imaging. In image-based insertion procedures motion of the patient's organs and tissues due to respiration behavior can have a significant impact, as the appearance and location of tissues are critical to properly analyze the scanned volume and determine the proper timing for inserting the medical instrument toward the target in the subject's body. Accordingly, imaging during the procedure, as well as instrument advancement, are to be executed at the same point/phase during the breathing cycle. According to some embodiments, respiration behavior of a patient may be presented to the user on the GUI, to enable the user to practice synchronizing imaging and insertion initiation with a certain point or phase of the respiration cycle. The respiration point/phase may be predetermined or it may be selected by the user. According to some embodiments, the presented respiration behavior is stored respiration behavior of a real patient. According to some embodiments, the presented respiration behavior is respiration behavior generated using data-based algorithm(s). According to some embodiments, visual illustrations (e.g., video, four-dimensional scans) may be displayed to the user to demonstrate tissue motion during the respiration cycle. The demonstrated tissue motion may be specific to the simulation case and the relevant region of interest.

According to some embodiments, at step 504, the method may include receiving user input regarding the locations of the target and the entry point on the displayed image. According to some embodiments, at step 506, the method may include determining if the locations marked by the user are optimal and/or valid. If it is determined that the target and entry point locations chosen/marked by the user are not optimal and/or are invalid, then at step 508, optimal/valid target and entry point locations may be marked on the displayed image by the processor. According to some embodiments, one or more algorithms (e.g., ML/DL algorithms) may determine the valid/optimal target and/or entry point location. According to some embodiments, an explanation may be presented to the user (visually and/or audibly) as to the considerations relating to the selection of the marked entry point and/or target location. Such considerations may be, for example: entry angle required for the instrument to reach the target starting from the entry point, limitations of the automated device (e.g., workspace limitations, registration constraints, etc.), limitations of the selected instrument for the simulation (e.g., instrument length, instrument flexibility which may affect the instrument's allowable maximal curvature, etc.), or any combination thereof. According to some embodiments, the method may include providing an explanation to the user as to why the entry point and/or target locations marked by him/her are invalid and/or are not optimal. According to some embodiments, at step 510, the method includes obtaining the user's confirmation to the target and entry point locations marked by the processor. According to some embodiments, the user may decide, at step 510, to change/adjust the target and entry point locations marked by the processor. According to some embodiments, the method may include presenting to the user the different considerations he/she should consider when marking the target and the entry point, and how these considerations may affect the calculation of the trajectory, without determining if the locations marked by the user are optimal and/or valid.

According to some embodiments, the user may mark, at step 504, in addition to the target and entry point locations, "no-fly" zones on the image-view, and if it is determined, at step 506, that the "no-fly" zones are invalid and/or not optimal, then valid/optimal "no-fly" zones" may be displayed, at step 508, for the user to confirm or edit, at step 510. According to some embodiments, valid/optimal "no-fly" zones may be identified using image processing methods and/or algorithm(s), such as ML/DL model(s), as disclosed, for example, in co-owned International Patent Application Publication No. WO 2021/214,750, which is incorporated herein by reference in its entirety. According to some embodiments, determining a "no-fly" zones map may be based on several parameters/considerations including but not limited to: patient anatomy, required/desired accuracy (e.g., the instrument's tip-to-target accuracy), steering duration and risk estimation. According to some embodiments, determining the "no-fly" zones may include a multi-loss scheme. For example, the loss function may be aimed to minimize the steering duration, maximize the accuracy and minimize the risk. According to some embodiments, the method may include presenting to the user (visually and/or audibly) the different parameters on which the determination of the displayed/recommended "no-fly" zone map was based and explaining the different considerations and the trade-off between the different parameters, so as to train the user how to better define "no-fly" zones in a real clinical procedure. According to some embodiments, the method may include allowing the user to adjust the weights (coefficients) used in the loss function to better understand the trade-off between the different parameters and the impact of the weight given to each parameter on the "no-fly" zone map, which may, in turn, impact the calculated trajectory. According to some embodiments, the user may adjust the weight given to each parameter according to the specific simulated procedure type (e.g., biopsy, fluid drainage, etc.), the target of the simulated procedure and/or his/her preferences. The adjustment may be using the user interface, via numerical fields and/or adjustable bars/scales. According to some embodiments, the method may include presenting to the user several optional "no-fly" zone maps, each option pertaining to different considered parameters and/or to different weights given to the different parameters. Such presentation may be used to train the user as to how to best determine the optimal "no-fly" zone map for each specific set of circumstances. According to some embodiments, the method may include presenting to the user the different considerations he/she should consider when selecting/marking the "no-fly" zones, and how they may affect the calculation of the trajectory, instead of determining if the "no-fly" zones marked by the user are optimal and/or valid.

If it is determined that the target and entry point locations (and, optionally, the "no-fly" zones) chosen/marked by the user are optimal/valid, or following the user's confirmation/change of the locations marked by the processor, a trajectory from the entry point to the target is calculated, at step 512.

According to some embodiments, at step 514, the method may include receiving user input regarding checkpoints along the calculated trajectory. According to some embodiments, the user may mark the checkpoints using the user interface (e.g., by clicking a computer mouse or tapping on the screen), and if it is determined, at step 516, that the marked checkpoints are invalid and/or are not optimal, then valid/optimal checkpoints may be displayed, at step 518, for the user to confirm or edit, at step 520. According to some embodiments, an upper and/or lower interval threshold between checkpoints may be predetermined. For example, it may be pre-set that the maximal allowable distance between each two checkpoints (or between the entry point and the first checkpoint and/or between the last checkpoint and the target) is 30 mm or 40 mm and/or that the minimal allowable distance between them is 2 mm or 3 mm or 4 mm or 5 mm. In such embodiments, if the user marks checkpoints at distances which exceed the upper threshold and/or fall below the lower threshold, the user's marking may be determined to be invalid. According to some embodiments, the invalid checkpoint(s) may be marked (e.g., by color) and/or an audio alert may be generated. According to some embodiments, default checkpoints may be set by the processor at default intervals (e.g., 20 mm), and the user can then confirm the marked default checkpoints or adjust the number of checkpoints and/or the distances between them. According to some embodiments, the optimal checkpoint locations may be determined using image processing methods and/or algorithm(s), such as ML/DL model(s), as disclosed, for example, in abovementioned International Patent Applications Publications Nos. WO 2021/214,750 and WO 2021/214,754. According to some embodiments, determining the checkpoints' number and locations may be based on several parameters/considerations, including but not limited to: patient anatomy, target size, target depth (distance from the entry point), desired/required accuracy (e.g., the instrument's tip-to-target accuracy), steering duration, total radiation dose and risk estimation. According to some embodiments, determining the checkpoints' distribution may include a multi-loss scheme. For example, the loss function may be aimed to minimize the steering duration, maximize the accuracy, minimize the total radiation dose and minimize the risk. According to some embodiments, the method may include presenting to the user the different parameters on which the determination of the optimal checkpoint locations was based and explaining the different considerations and the trade-off between the different parameters, so as to train the user how to better mark checkpoints along the planned trajectory in a real clinical procedure. According to some embodiments, the method may include allowing the user to adjust the weights (coefficients) used in the loss function to better understand the trade-off between the different parameters and the impact of the weight given to each parameter on the optimal checkpoint distribution. According to some embodiments, the user may adjust the weight given to each parameter according to the specific simulated procedure type (e.g., biopsy, fluid drainage, etc.), the target of the simulated procedure and/or his/her personal preferences. The adjustment may be using the user interface, via numerical fields and/or adjustable bars/scales. According to some embodiments, the method may include presenting to the user several optional checkpoint distributions, each option pertaining to different considered parameters and/or to different weights given to the different parameters. Such presentation may be used to train the user as to how to best determine the optimal checkpoint distribution for each specific set of circumstances. According to some embodiments, the method may include explaining to the user why the checkpoint locations chosen/marked by him/her are invalid and/or are not optimal. According to some embodiments, the method may include presenting to the user the different considerations he/she should consider when marking checkpoints along the trajectory, without determining if the checkpoints marked by the user are optimal and/or valid.

If it is determined that the checkpoints marked by the user are valid and optimal, or following the user's confirmation/change of the locations marked by the processor then, at step 522, the method includes executing instrument insertion and/or steering, according to the planned trajectory. According to some embodiments, the insertion and/or steering of the instrument is executed upon initiation by the user. Such initiation may simulate the user pressing an activation pedal (e.g., a foot pedal) and/or button, either from within the procedure room of from a remote location (e.g., the control room or a location external to the medical facility) using a remote control unit, in a real clinical procedure. According to some embodiments, the simulator system may include such a pedal/button which the user is required to press to initiate the advancement of the virtual (or tangible) instrument. According to some embodiments, stored respiration behavior of a patient may be presented to the user on the GUI, to allow (or prompt) the user to initiate instrument advancement at the same point or phase of the respiration cycle as the point or phase of the respiration cycle in which previous imaging and/or previous insertion steps were initiated (for example, as described in step 502 hereinabove).

According to some embodiments, the advancement of the medical instrument is carried out in a 2D plane. According to some embodiments, the advancement of the medical instrument is carried out in a 3D space. According to some embodiments, and as described in greater detail elsewhere herein, the method may include implementing an algorithm configured to simulate the advancement of the medical instrument based, at least in part, on data associated with the type of tissue, the type of procedure, the type of selected medical instrument and/or medical characteristics of the selected virtual patient. According to some embodiments, the algorithm may assess in real-time if the medical instrument has deviated from the planned trajectory. According to some embodiments, certain deviations of the medical instrument from the planned trajectory may be automatically addressed by the processor via automatic adjustment of the trajectory as disclosed, for example, in abovementioned U.S. Pat. No. 8,348,861. According to some embodiments, certain deviations of the medical instrument from the planned trajectory, for example deviations which exceed a predetermined threshold, may require the user to initiate a trajectory update, i.e., recalculation of the trajectory for the remainder of the procedure, as described in further detail elsewhere herein.

According to some embodiments, at step 524, the method may include displaying, on the image-view, the instrument at the next checkpoint (or at the target, if the target has been reached). According to some embodiments, prior to such displaying, the user may be prompted to initiate imaging. According to some embodiments, stored respiration behavior of a patient may be presented to the user on the GUI, to allow the user to initiate the imaging at the same point or phase of the respiration cycle as the point or phase of the respiration cycle in which previous imaging and insertion steps were initiated (for example, as described in steps 502 and 522). According to some embodiments, step 524 may further include determining the real-time position of the medical instrument, the target, and optionally other regions of interest, such as previously determined "no-fly" zones. According to some embodiments, movement of the target may be included in stored image view/s and/or animation segments, for example, when such movement occurred in the actual procedure upon which the simulated case is based. According to some embodiments, the movement of the tissue/target may be created in real-time by algorithm(s) implemented in the simulator, which may include ML/DL capabilities, such that the simulated movement is a direct result of the advancement of the virtual instrument according to the trajectory planned by the user in the specific simulation session. According to some embodiments, the simulation may be executed using a real robot, instrument and imaging system, together with a phantom device, such that actual target movement within the phantom may occur during the simulation.

According to some embodiments, at step 526, the method includes determining if the instrument has reached the target. If the target has been reached, the simulation ends, at step 528, whereas if the target has not yet been reached, the simulation continues. If the target has not moved from its previous location, steps 522-526 are repeated according to the planned trajectory. If, however, the target has moved from its previous location, then the method includes, at step 530, receiving user input regarding the updated target location followed by calculation/displaying of an updated trajectory. According to some embodiments, for example embodiments in which the movement of the target is pre-set for the specific simulation session, the updated trajectory may be pre-set accordingly, such that stored images and/or animations showing the updating of the trajectory may be displayed on the monitor. According to some embodiments, the updated trajectory may be calculated in real-time, based on simulated target movement (i.e., using AI algorithm(s)) or actual target movement (i.e., in case of actual target movement within a phantom). According to some embodiments, the simulator may include ML/DL algorithm(s) which can predict the future movement of the target and update the trajectory to facilitate the medical instrument reaching the target at its predicted end-point location. According to some embodiments, recalculation of the trajectory may further be required if, for example, an obstacle is identified along the trajectory during execution of instrument insertion. According to some embodiments, the obstacle may be an obstacle which was marked/identified prior to the calculation of the trajectory but tissue movement resulting from the advancement of the instrument within the tissue caused the obstacle to move such that it has entered the planned path. According to some embodiments, the obstacle may be a new obstacle, i.e., an obstacle which was not visible in the image-view based upon which the trajectory was calculated and became visible during the simulation procedure. According to some embodiments, the user may be prompted to confirm the recalculated trajectory before resuming the advancement of the instrument (e.g., to the next checkpoint) according to the updated trajectory. According to some embodiments, after the trajectory has been updated, steps 522-526 (and, optionally, step 530) are repeated until the target is reached and the simulation then ends. According to some embodiments, the method includes generating an animation associated with the recalculation of the trajectory and the advancement of the medical instrument according to the updated trajectory.

Figure 6A:
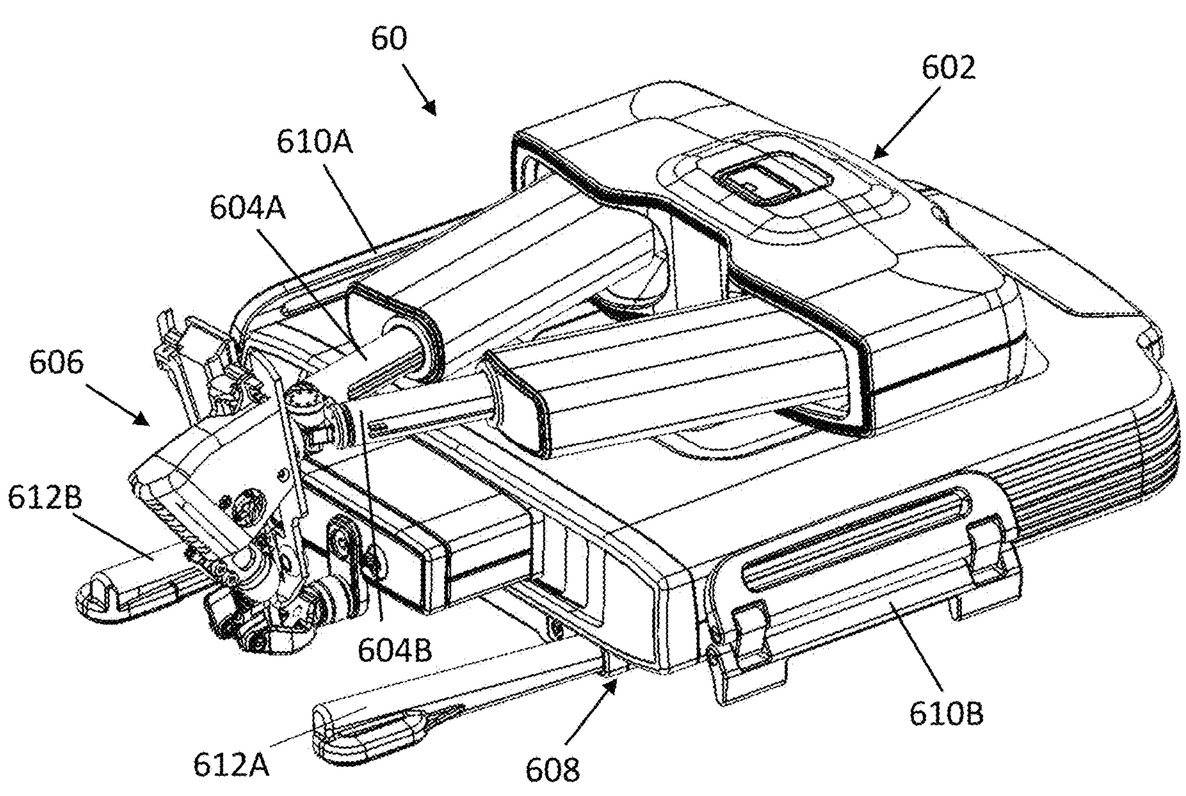
FIGS. 6A-6B show perspective views of an exemplary robotic device (FIG. 6A) and an exemplary console (FIG. 6B) of a robotic system for inserting and/or steering a medical instrument toward an internal target, the operation of which may be simulated using the disclosed simulation methods and systems, in accordance with some embodiments of the present disclosure.
Figure 6B:
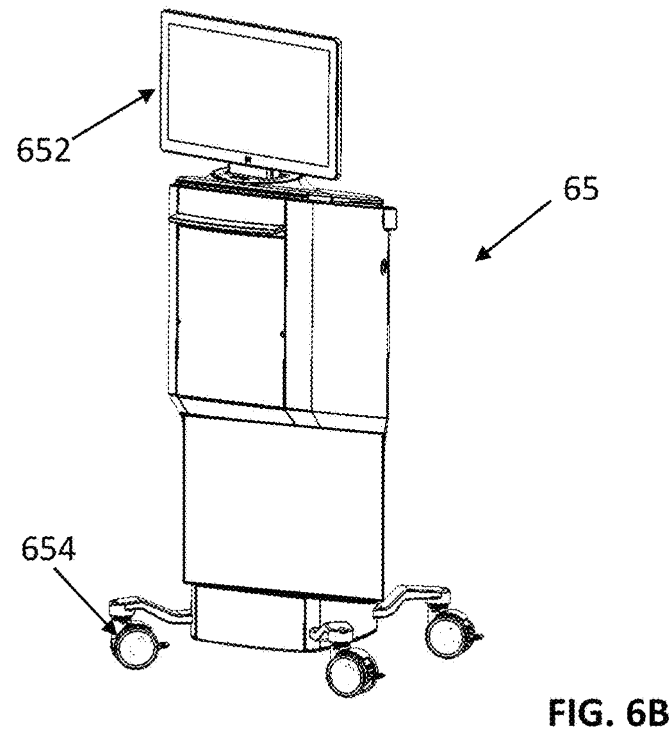

Reference is now made to FIGS. 6A-6B, which show an exemplary automated system the operation of which may be simulated using the disclosed methods and systems, according to some embodiments. FIG. 6A shows an exemplary automated (robotic) medical device 60 for inserting and steering a medical instrument in a body of a subject. The device 60 may include a housing 602 accommodating therein at least a portion of the steering mechanism. The steering mechanism may include at least one moveable platform (not shown) and at least two moveable arms 604A and 604B, configured to allow or control movement of an end effector 606, at any one of desired movement angles or axis, as disclosed, for example, in abovementioned U.S. Patent Application Publication No. 2019/290,372. The moveable arms 604A and 604B may be configured as piston mechanisms. A suitable medical instrument (not shown) may be connected to the end effector 606, either directly or by means of a suitable insertion module, such as the insertion module disclosed in abovementioned U.S. Pat. No. 11,083,488. The medical instrument may be any suitable instrument capable of being inserted and steered within the body of the subject, to reach a designated target, wherein the control of the operation and movement of the medical instrument is effected by the end effector 606. The end effector 606 may include a driving mechanism (also referred to as "insertion mechanism"), or at least a portion thereof, which is configured to advance the medical instrument toward the target. The end effector 606 may be controlled by a suitable control system, as detailed herein.

According to some embodiments, the medical instrument may be selected from, but not limited to: a needle, probe (e.g., an ablation probe), port, introducer, catheter (such as a drainage needle catheter), cannula, surgical tool, fluid delivery tool, or any other suitable insertable tool configured to be inserted into a subject's body for diagnostic and/or therapeutic purposes. In some embodiments, the medical tool includes a tip at the distal end thereof (i.e., the end which is inserted into the subject's body). The tool tip may be a diamond tip, a bevel tip, a conical tip, etc.

According to some embodiments, the device 60 may have a plurality of degrees of freedom (DOF) in operating and controlling the movement the of the medical instrument along one or more axis. For example, the device may have up to six degrees of freedom. For example, the device may have at least five degrees of freedom. For example, the device may have five degrees of freedom, including two linear translation DOF (in a first axis), a longitudinal linear translation DOF (in a second axis substantially perpendicular to the first axis) and two rotational DOF. For example, the device may have forward-backward and left-right linear translations facilitated by two moveable platforms, front-back and left-right rotations facilitated by two moveable arms (e.g., piston mechanism), and longitudinal translation toward the subject's body facilitated by the insertion mechanism. According to some embodiments, the control system (i.e., processor and/or controller) may be capable of controlling the steering mechanism (including the moveable platforms and the moveable arms) and the insertion mechanism simultaneously, thus enabling non-linear steering of the medical instrument, i.e., enabling the medical instrument to reach the target by following a non-linear trajectory. According to some embodiments, the device may have six degrees of freedom, including the five degrees of freedom described above and, in addition, rotation of the medical instrument about its longitudinal axis. According to some embodiments, rotation of the medical instrument about its longitudinal axis may be facilitated by a designated rotation mechanism. In some embodiments, the control system (i.e., processor and/or controller) may be capable of controlling the steering mechanism, the insertion mechanism and the rotation mechanism simultaneously.

According to some embodiments, the device may further include a base 608, which allows positioning of the device on or in close proximity to the subject's body. According to some embodiments, the device may be configured for attachment to the subject's body either directly or via a suitable mounting surface, such as the mounting base disclosed in abovementioned U.S. Pat. No. 11,103,277, or the attachment apparatus disclosed in abovementioned U.S. Patent Application Publication No. 2021/228,311. Attachment of the device to the mounting surface may be carried out using dedicated latches, such as latches 610A and 610B. According to some embodiments, the robotic device may be couplable to a dedicated arm or base which is secured to the patient's bed, to a cart positioned adjacent the patient's bed or to an imaging device (if used), and held on the subject's body or in close proximity thereto, as described, for example, in abovementioned U.S. Pat. Nos. 10,507,067 and 10,639,107.

According to some embodiments, the device 60 may include electronic components and motors (not shown) allowing the controlled operation of the device in inserting and steering the medical instrument. According to some exemplary embodiments, the device may include one or more Printed Circuit Board (PCB) (not shown) and electrical cables/wires (not shown) to provide electrical connection between a controller (not shown) and the motors of the device and other electronic components thereof. According to some embodiments, the controller may be embedded, at least in part, within device 60. According to some embodiments, the controller may be a separate component. In some embodiments, the device may include a power supply (e.g., one or more batteries) (not shown). According to some embodiments, the device may be configured to communicate wirelessly with the controller and/or processor.

According to some embodiments, the device may further include registration elements disposed at specific locations on the device 60, such as registration elements 612A and 612B, for registration of the device to the image space, in image-guided procedures. In some embodiments, registration elements may be disposed on the mounting surface to which device may be coupled, either instead or in addition to registration elements disposed on device. According to some embodiments, registration of the device to the image space may be carried out via image processing of one or more components of the device, such as the end effector, and/or of the mounting surface (or at least a portion thereof), which are visible in generated images.

According to some embodiments, device 60 is part of a system for inserting and/or steering a medical instrument in a subject's body. The system may include the steering and insertion device, as disclosed herein, and a control unit (or—"workstation" or "console") configured to allow control of the operating parameters of device. According to some embodiments, the user may operate the device 60 using a pedal or an activation button. According to some embodiments, the user may operate the device using voice commands.

Reference is now made to FIG. 6B, which shows an exemplary console 65 of an insertion and/or steering system, according to some embodiments. The console 65 may include a display 652 and a user interface (not shown). In some embodiments, the user interface may be in the form of buttons, switches, keys, keyboard, computer mouse, foot pedal/switch, joystick, touch-sensitive screen, and the like. The monitor and user interface may be two separate components, or they may form together a single component (e.g., in the form of a touch-screen). The console 65 may include one or more suitable processors (for example, in the form of a PC) and one or more suitable controllers, configured to physically and/or functionally interact with device 60, to determine and control the operation thereof. The one or more processors may be implemented in the form of a computer (such as a workstation, a server, a PC, a laptop, a tablet, a smartphone or any other processor-based device). In some embodiments, the console may be portable (e.g., by having wheels 654 or being placed on a movable platform).

According to some embodiments, the system may include a remote control unit, which may enable the user to activate the device from a remote location, such as the control room adjacent the procedure room, a different location in the medical facility or a location external to the medical facility. According to some embodiments, the remote control unit may duplicate the automated system's robot controller. According to some embodiments, the remote control unit may duplicate the automated system's user interface. For example, the remote control unit may include an activation button/switch which may enable activation of the robotic device similarly to the foot pedal located inside the procedure room. The remote control unit may further include one or more of: a monitor, a touchscreen, a joystick, a computer mouse and a keyboard. The remote control unit may further include an emergency stop button, to allow the user to stop the procedure immediately in case of an emergency. According to some embodiments, the remote control unit may duplicate the automated system's GUI, to enable planning and/or monitoring of the procedure from outside the procedure room. The remote control unit may communicate with the system's console either in a wired manner (e.g., using one or more cables) or wirelessly. According to some embodiments, the user may use the remote control unit(s) to plan and execute several procedures simultaneously. According to some embodiments, the disclosed simulator systems and method may include training and/or allowing users to practice planning and/or executing and/or monitoring two or more insertion/steering procedures simultaneously.

In some embodiments, the one or more processors may be configured to perform one or more of: determine the location of the target; determine the predicted location of the target during and/or at the end of the procedure (end-point), determine (plan) a trajectory for the medical instrument to reach the target (for example, at the predicted location of the target); update the trajectory in real-time, for example due to movement of the target from its initial identified position as a result of the advancement of the medical instrument within the patient's body, respiration motion or patient movements; present the planned and/or updated trajectory on the monitor 652; control the movement (insertion/steering) of the medical instrument based on the planned and/or updated trajectory by providing executable instructions (directly or via the one or more controllers) to the device; determine the actual location of the medical instrument (e.g., the tip thereof) using image processing and/or by performing required compensation calculations; receive, process and visualize on the monitor images or image-views created from a set of images (between which the user may be able to scroll), operating parameters and the like; or any combination thereof.

According to some embodiments, the planned trajectory of the medical instrument (in particular, the tip thereof) may be calculated based on a predicted location of the target within the subject body and optionally, inter alia, based on one or more inputs from the user, such as the entry point, areas to avoid en route (obstacles or "no-fly" zones), which the user marks on at least one of the obtained images. In some embodiments, the processor may be further configured to identify the target, actual location of the target, predicted location of the target, the obstacles and/or the insertion/entry point. In some embodiments, data-analysis algorithms, e.g., AI-based models, may be used by the processor to perform such identifications/calculations. According to some embodiments, during the operation of the system, various types of data may be generated, accumulated and/or collected, for further use and/or manipulation. Such collected datasets may be collected from one or more systems, operating under various circumstances (for example, different procedures, different medical instruments, different patients, different locations and operating staff, etc.), to thereby generate a large data base ("big data"), that can be used, utilizing suitable data analysis tools and/or AI-based tools to ultimately generate models or algorithms that allow performance enhancements, automatic control or affecting control (i.e., by providing recommendations), of the medical systems. Thus, by generating such advantageous and specialized models or algorithms, enhanced control and/or operation of the system may be achieved.

In some embodiments, the system may be configured to operate in conjunction with an imaging system, including, but not limited to: X-Ray, CT, cone beam CT, CT fluoroscopy, MRI, ultrasound, or any other suitable imaging modality.

According to some embodiments, the disclosed simulation methods may include assessing the procedure during the simulation, so as to assess the performance of the user. According to some embodiments, assessing the procedure may include applying at least one of the calculated trajectory, the confirmed checkpoints, the marked and/or selected obstacles, and the selected target point to an algorithm configured to assess the procedure during advancement of the medical instrument. According to some embodiments, assessing the procedure may include assessing if the trajectory became invalid or unsafe to the patient during the simulated procedure due to, for example, the appearance of new potential obstacles which were not identified by the user, a change in the position of the target, a change in the curvature of the trajectory (e.g., as a result of a trajectory update) which exceeds the maximal allowable curvature, etc. According to some embodiments, the simulator may alert the user during the simulation when a result of an assessment is that the trajectory has become invalid or unsafe for the patient, to allow the user to apply appropriate correction actions, such as add one or more checkpoints along the trajectory, mark the new obstacle and/or new position of the target, and initiate an update of the trajectory, etc. According to some embodiments, the simulator does not alert the user during the simulation and the results of the assessment are used to calculate a final assessment (or score) for the simulation session once the session is completed. The score may be used to assess the performance of the user and/or the user's readiness to perform actual procedures, for example, if the simulation sessions are part of an initial training program.

According to some embodiments, assessing the procedure may include identifying the trajectory and/or the procedure as having an on-target and/or off-target status.

According to some embodiments, an on-target status may include any one or more of having a high percent chance of reaching the target (e.g., above 97%), having a high percent chance of success (e.g., above 94%), being on a trajectory rout identified as optimal for the specific current procedure, and the like. According to some embodiments, an off-target status may include any one or more of having a low percent chance of reaching the target (e.g., below 85%), having a low percent chance of success (e.g., below 75%), being on a trajectory rout identified as not-optimal for the specific current procedure, and the like.

According to some embodiments, the method may include outputting a rank/score (such as a score ranging between 1 and 10) associated with an assessment of a completed procedure simulation. According to some embodiments, the method may include generating and/or analyzing statistics associated with one or more simulations, for example, one or more simulations relating to a same user and/or a same organization. According to some embodiments, the statistics may include, for example, an average rank/score, planning time, accuracy, and number of failed/invalid trajectories during the simulation.

Figure 7A:
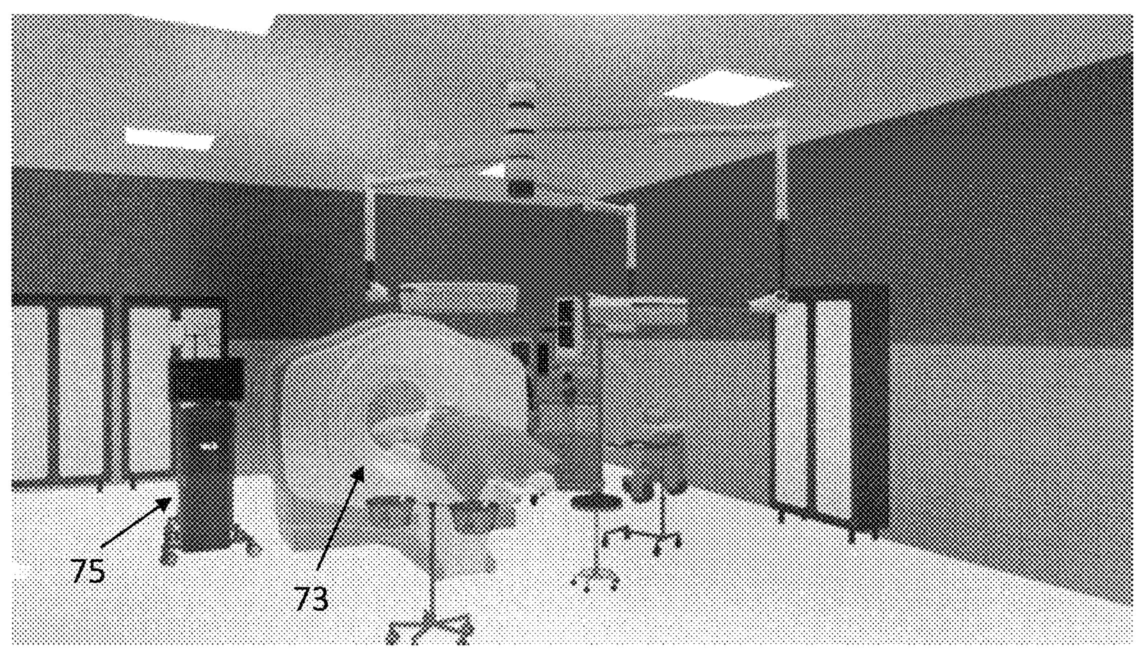
FIGS. 7A-7N show screenshots of an exemplary simulation session performed using the disclosed simulation methods and systems, including image-views and animation segments displayed to the user, in accordance with some embodiments of the present disclosure.
Figure 7B:
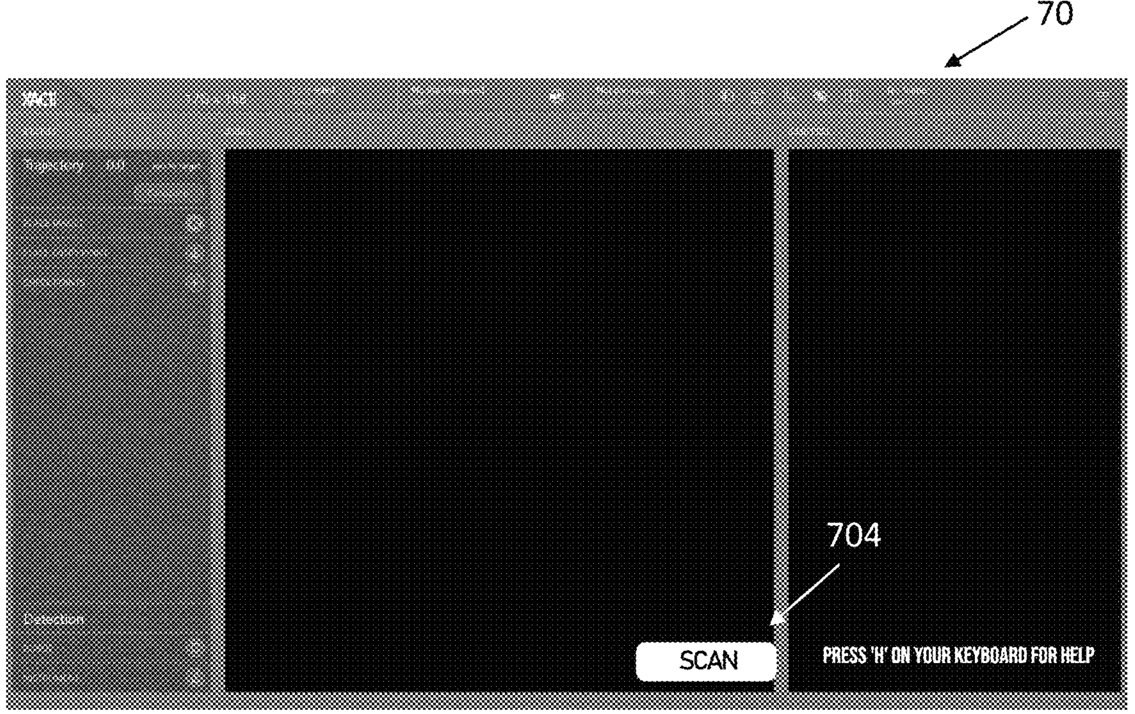
Figure 7C:
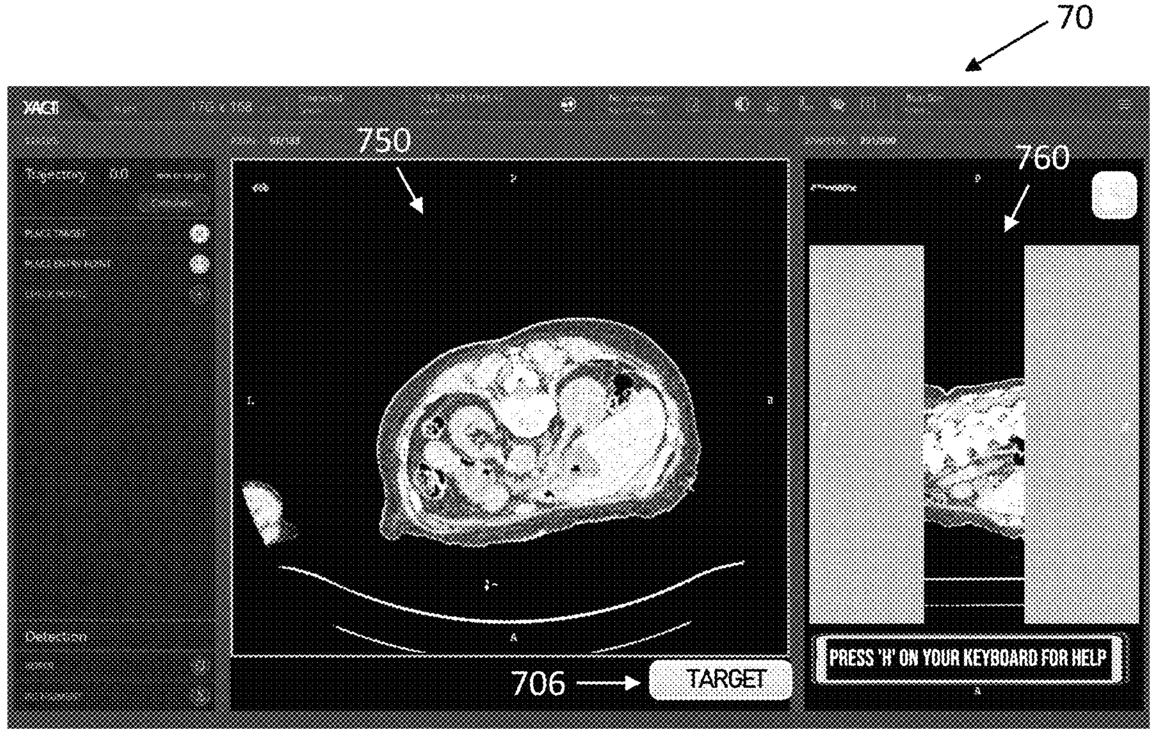
Figure 7D:
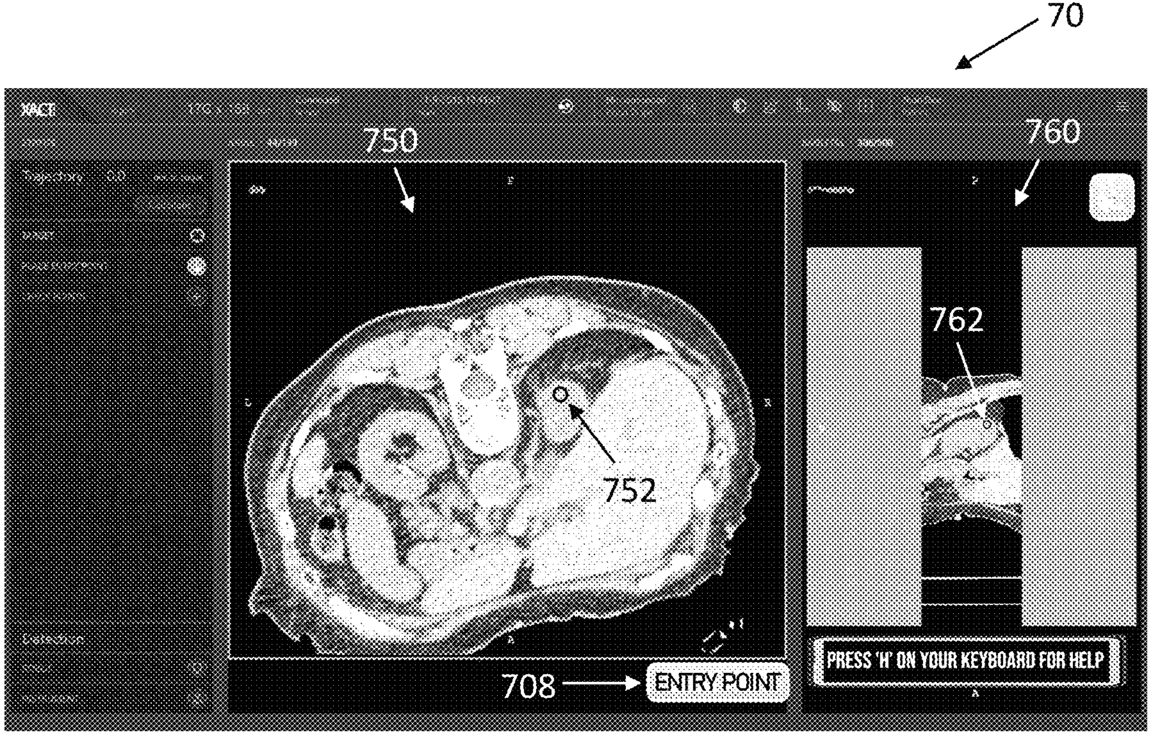
Figure 7E:
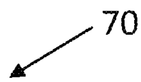
Figure 7E:
Figure 7F:
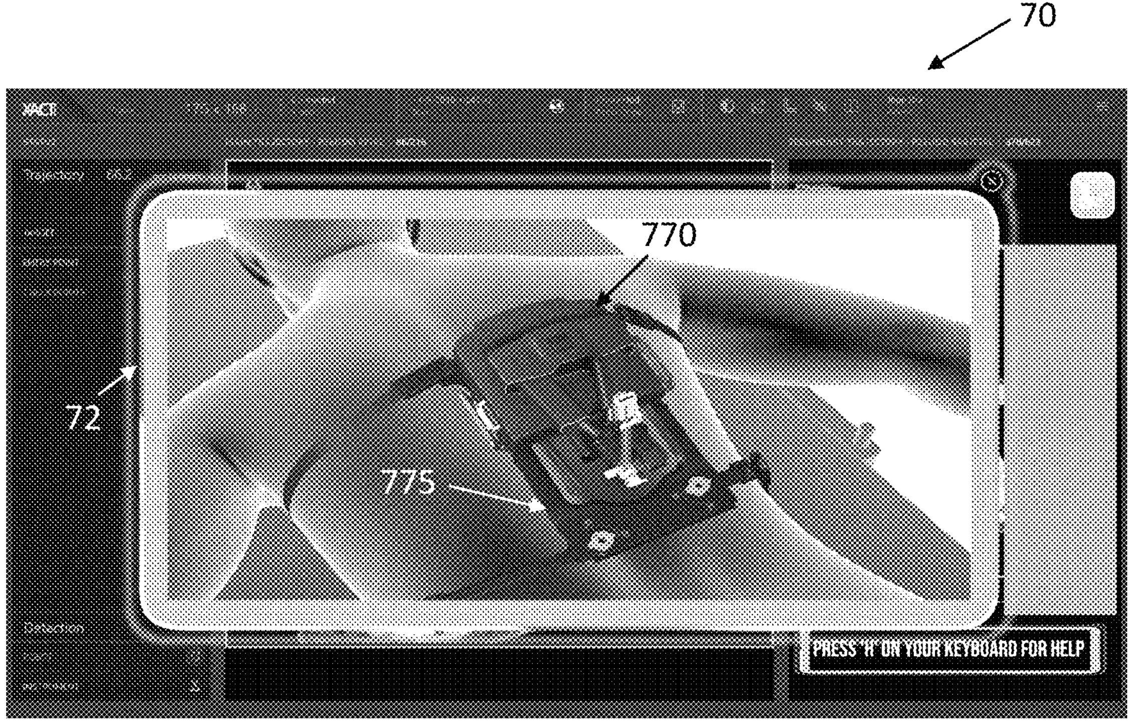
Figure 7G:
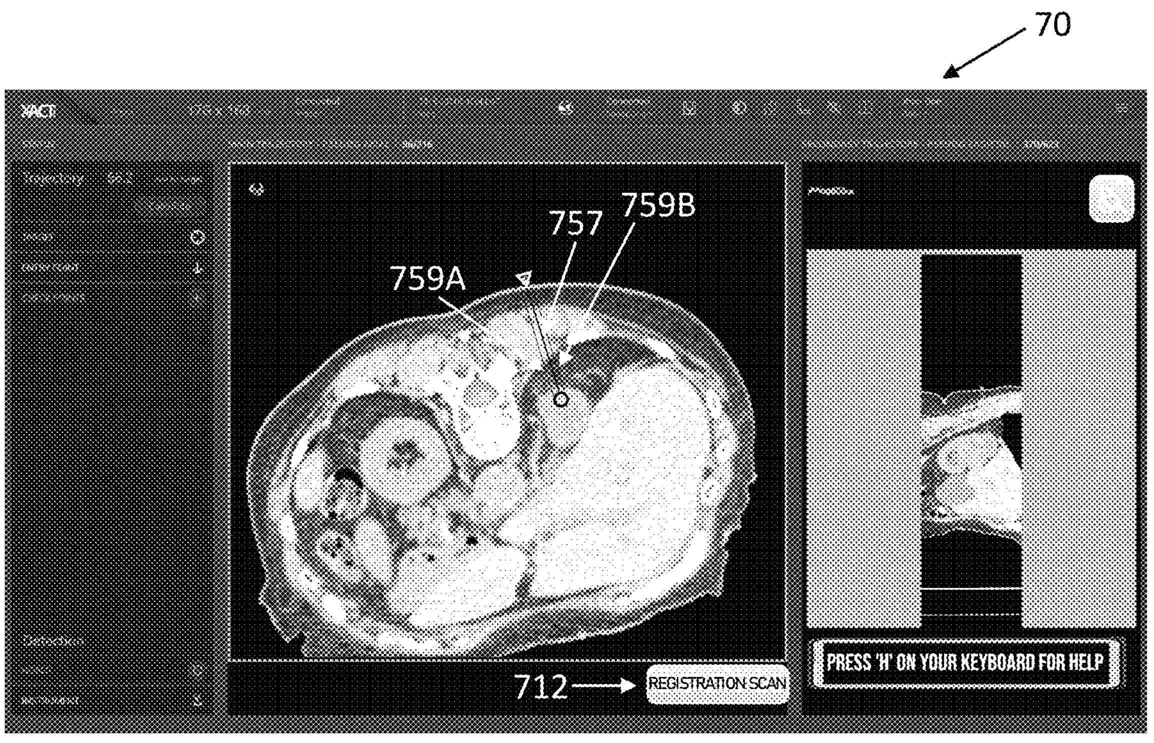
Figure 7H:
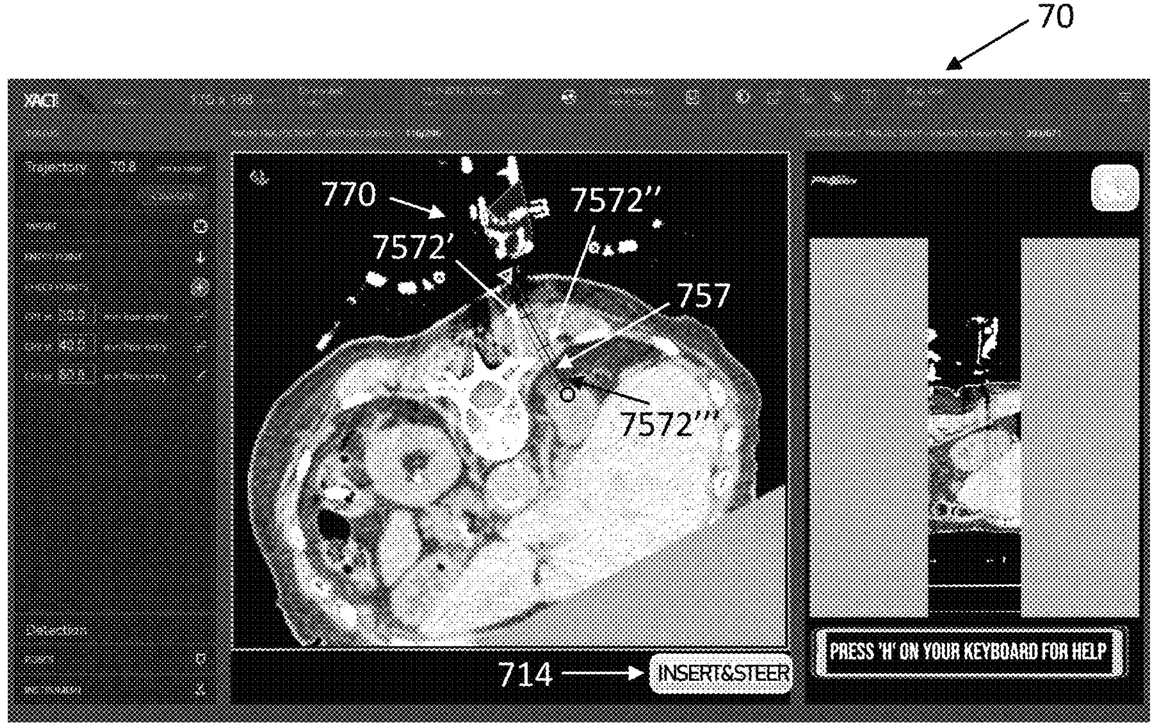
Figure 7I:
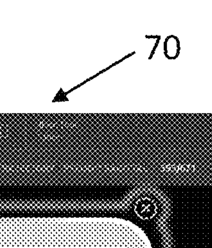
Figure 7I:
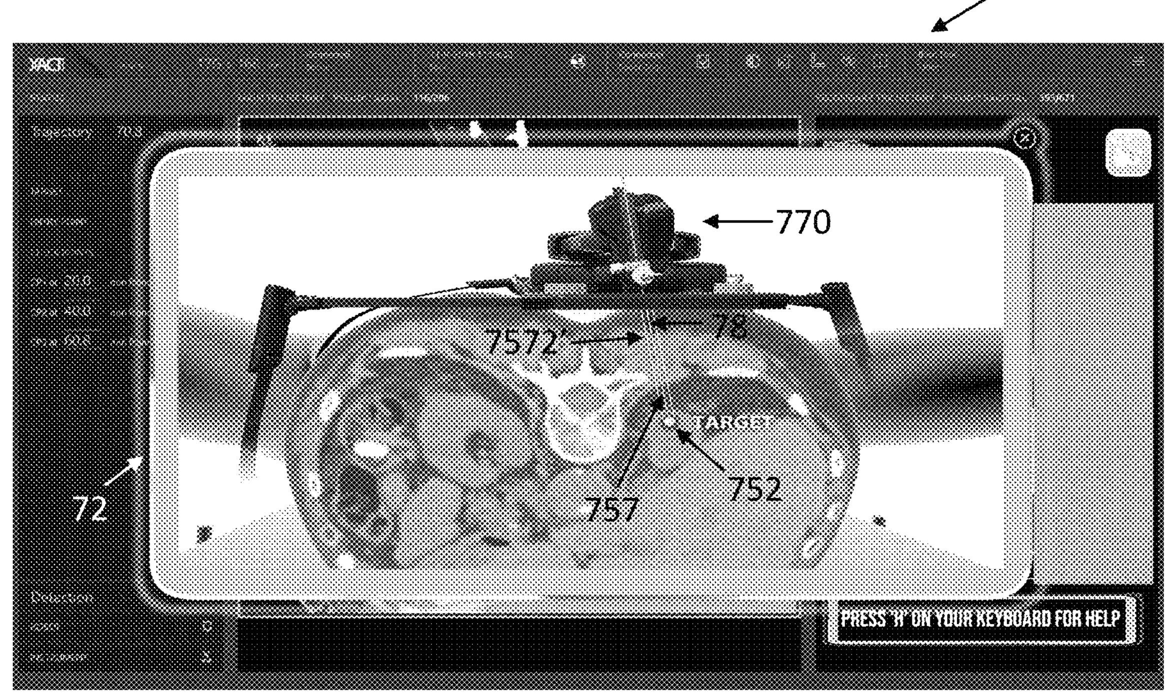
Figure 7J:
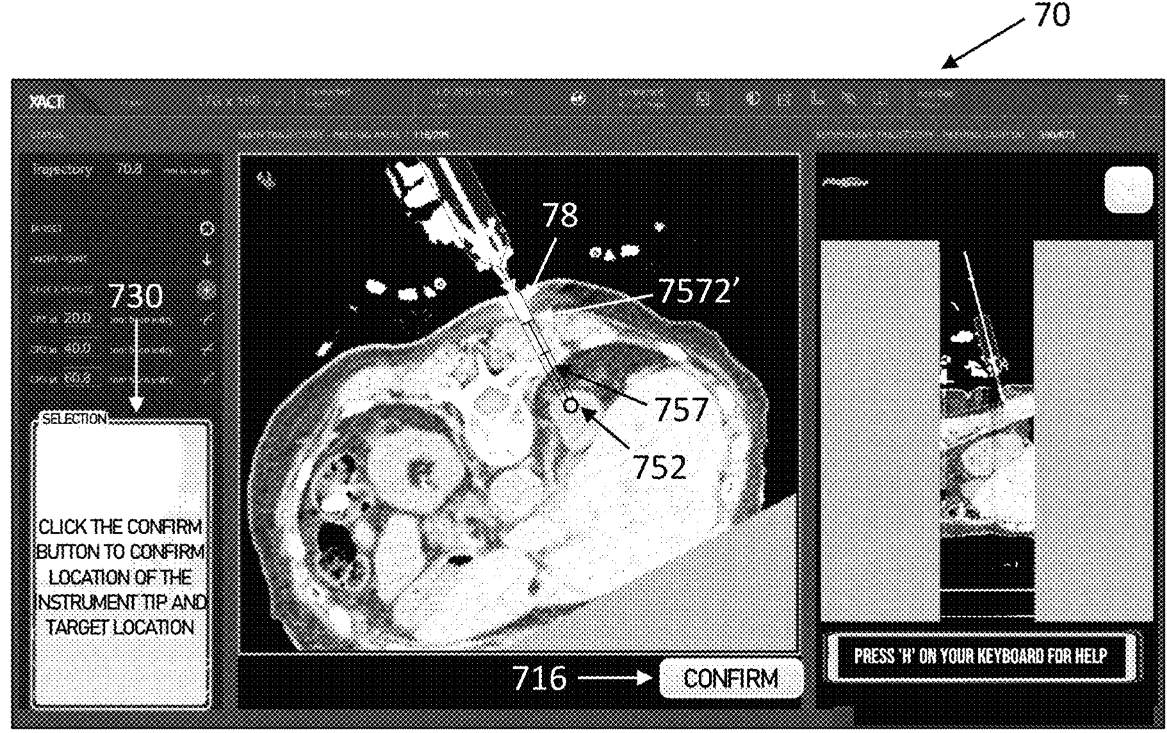
Figure 7K:
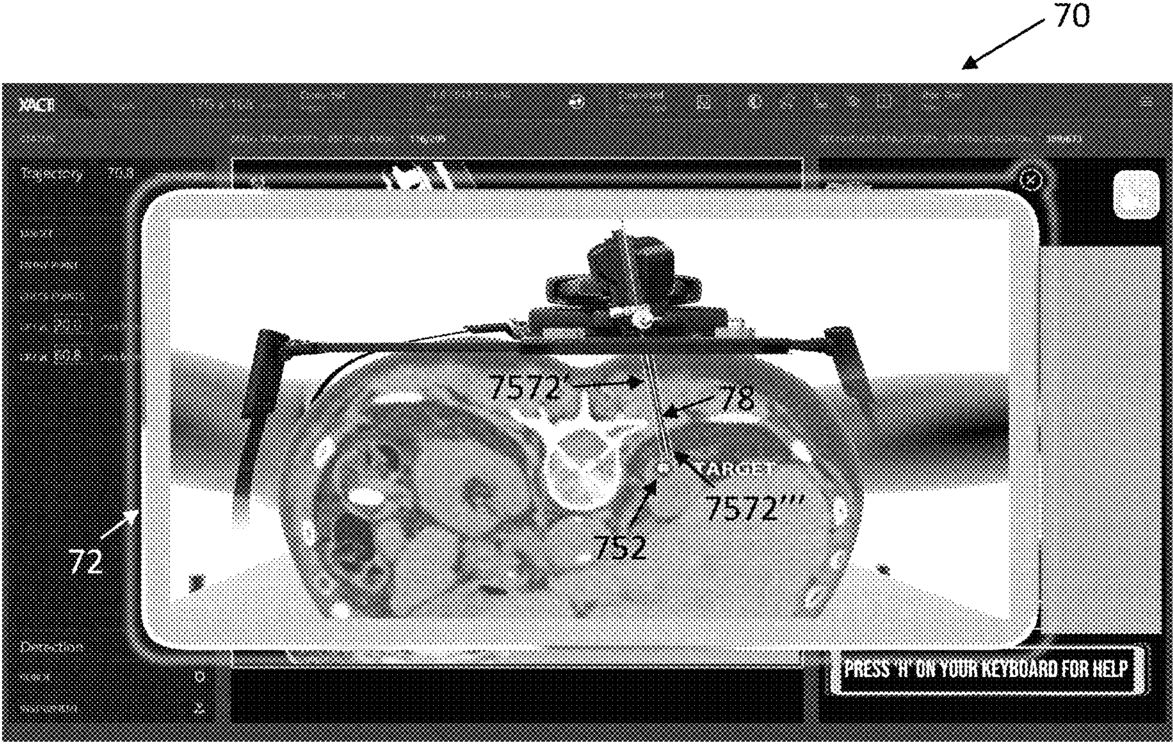
Figure 7L:
Figure 7M:
Figure 7M:
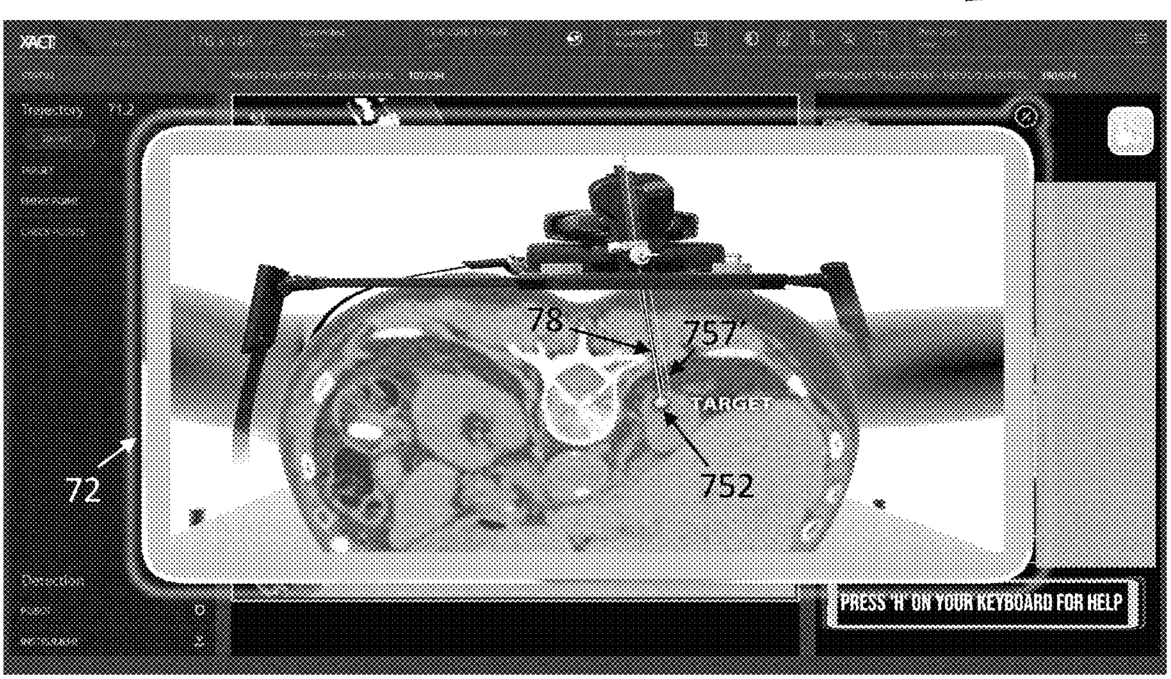
Figure 7N:
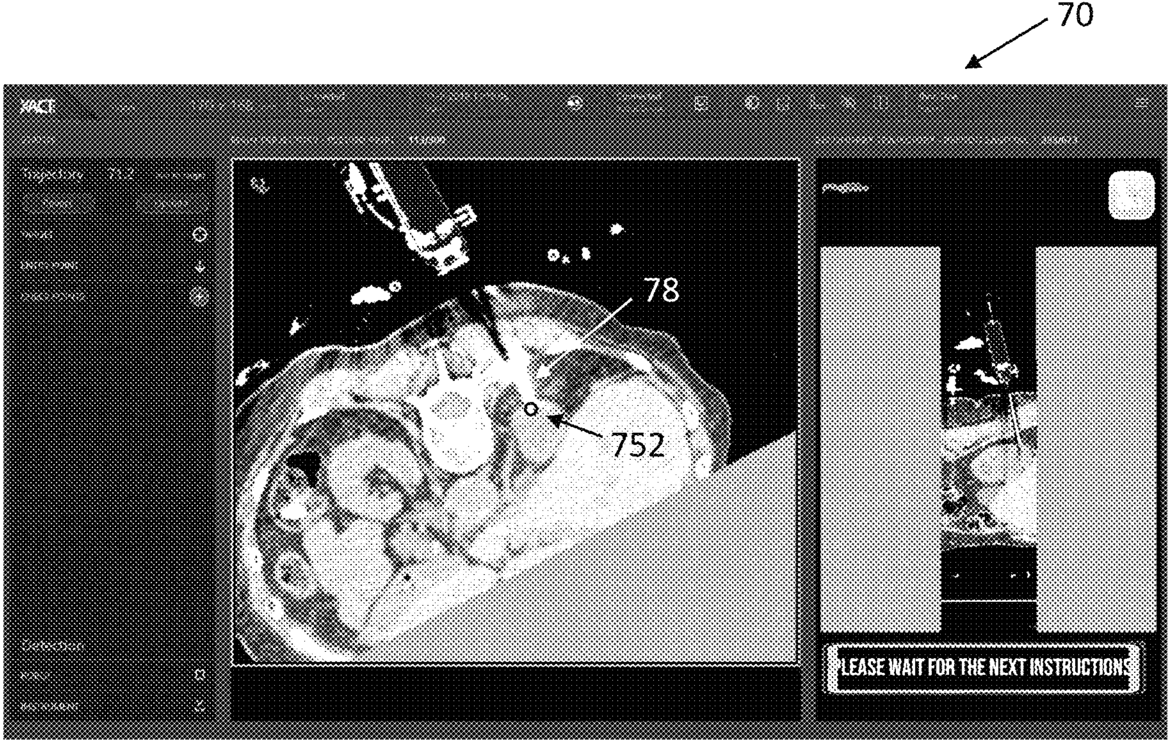

FIGS. 7A-7N show screenshots of an exemplary simulation session performed using an exemplary simulator, including the image-views and animation segments displayed to the user, according to some embodiments. FIG. 7A is a screenshot of an animation showing a patient lying on a patient bed in a procedure room. In this example, the patient is in a CT procedure room, ready to be inserted into the CT gantry 73 for initial scanning. Also shown is a console 75 of a robotic system positioned next to the patient.

FIG. 7B is a screenshot of a GUI 70 of the simulator's software application presented on a monitor, for example display 104 shown in FIG. 1. According to some embodiments, the SW application implemented in the simulator is the actual clinical SW application of the automated system which is used during clinical procedures. According to some embodiments, the SW application implemented in the simulator is a dedicated SW application resembling the clinical software application. In FIG. 7B, a "SCAN" button 704 is shown on the screen. According to some embodiments, the user can initiate imaging, in this case, a CT scan, of a region of interest, by clicking "SCAN" button 704, e.g., using a computer mouse. According to some embodiments, the simulator includes a plurality of images of various regions in the body stored in the simulator's memory module and/or a local server and/or a remote server and/or cloud. The stored images may be obtained from actual previously executed medical procedures or they may be general (empty) images of different body regions. According to some embodiments, clicking the "SCAN" button 704 results in one or more of the stored images (or image-views), according to the selected procedure/case to be simulated, to be shown on the monitor. According to some embodiments, the simulation may be executed using a real robot or a demo version of the robot, a phantom device, and a real imaging system. In such embodiments, actual imaging may be initiated by clicking the "SCAN" button 704.

FIG. 7C is a screenshot of GUI 70 with two image-views of a region of interest presented; an axial view 750 (left) and a sagittal view 760 (right). In FIG. 7C, a "TARGET" button

706 is shown on the screen. According to some embodiments, clicking the "TARGET" button 706 results in the target to be automatically marked, either based on a specific stored procedure or using image processing and/or a data-based algorithm. In such embodiments, the user may be allowed to change the location of the target as determined (recommended) by the simulator (i.e., the simulator's processor). According to some embodiments, clicking the "TARGET" button 706 enables the user to manually mark the target on the image-view (e.g., using the computer mouse). For example, a target icon (not shown) may appear on the screen, which the user can place on the target as he/she identifies it on the image-view.

FIG. 7D is a screenshot of GUI 70 with the axial and sagittal image-views 750 and 760, with the target 752 and 762 respectively, marked thereon. In FIG. 7D, an "ENTRY POINT" button 708 is shown on the screen. According to some embodiments, clicking the "ENTRY POINT" button 708 results in the entry point to be automatically marked, either based on a specific stored procedure or using algorithm(s) which calculate the optimal entry point location for the simulated procedure. In such embodiments, the user may be allowed to change the location of the entry point as determined (recommended) by the simulator (i.e., the simulator's processor). In some such embodiments, the parameters making the marked entry point optimal may be presented to the user, either visually or audibly. According to some embodiments, clicking the "ENTRY POINT" button 708 enables the user to manually mark the entry point on the image-view (e.g., using the computer mouse). For example, an entry point icon (not shown) may appear on the screen, which the user can place on the entry point (on the image-view) he/she selects for the simulated procedure. According to some embodiments, the user may be prompted to mark also obstacle(s) on the image view, for example by means of an "OBSTACLES" button (not shown). In such embodiments, the user may either mark the obstacle(s) manually, or initiate automatic marking by the simulator, either based on a specific stored procedure or using algorithm(s) which identify the obstacle(s) in the image-view.

FIG. 7E is a screenshot of GUI 70 with the target 752, 762 and entry point 754, 764 marked on the axial and sagittal image-views. According to some embodiments, as shown for example in FIG. 7E, once both the target and the entry point have been marked on the image-view, a default linear trajectory 756 from the entry point 754 to the target 752 may be presented on the image-view. According to some embodiments, as shown for example in FIG. 7E, default safety margins 758A and 758B on either side of the trajectory may also be presented. In FIG. 7E, a "CALCULATE" button 710 is shown on the screen. According to some embodiments, clicking the "CALCULATE" button 710 results in a trajectory to be automatically presented on the image-view(s) based on a specific stored procedure. According to some embodiments, the trajectory is calculated in real-time (i.e., during the simulation session) using algorithm(s) which calculate the optimal trajectory for the simulated procedure.

FIG. 7F is a screenshot of GUI 70 and an animation window 72, which shows an animation of a patient lying on the patient bed with an automated device 770, for example automated device 60 shown in FIG. 6A, attached to the patient's body. According to some embodiments, as shown in FIG. 7F, the automated device 770 may be attached to the patient's body using an attachment apparatus 775, such as the mounting base/attachment frame disclosed in abovementioned U.S. Pat. No. 11,103,277 or U.S. Patent Application Publication No. 2021/228,311.

FIG. 7G is a screenshot of GUI 70 after calculation of the trajectory (or marking of a stored trajectory). In the example shown in FIG. 7C, the calculated trajectory 757 is the same as the default trajectory 756 presented in FIG. 7E, and the determined safety margins 759A and 759B are the same as the default safety margins presented in FIG. 7E. In FIG. 7G, a "REGISTRATION SCAN" button 712 is shown on the screen, whereas the user can initiate a registration scan, in this case a CT scan, by clicking the "REGISTRATION SCAN" button 712, e.g., using a computer mouse. A registration scan is initiated in order to register the robotic device to the image space, after the device has been attached to the patient, as shown in FIG. 7F, or positioned in close proximity to the patient, e.g., using a dedicated arm. According to some embodiments, the simulator includes a plurality of images of various regions in the body, which include the robotic device, stored in the simulator's memory module and/or a local server and/or a remote server and/or cloud. The stored images may be obtained from actual previously executed medical procedures or they may be general (empty) images. According to some embodiments, clicking the "REGISTRATION SCAN" button 712 results in one or more of the stored images (or image-views), according to the selected procedure/case to be simulated, to be shown on the monitor. According to some embodiments, the simulation may be executed using a real robot or a demo version of the robot, a phantom device, and a real imaging system. In such embodiments, actual imaging may be initiated by clicking the "REGISTRATION SCAN" button 712.

FIG. 7H is a screenshot of GUI 70 following the registration scan, with the robot 770 visible in the image-views. Also shown in FIG. 7H is the planned trajectory 757 with checkpoints marked thereon. In the shown example, three checkpoints 7572', 7572" and 7572'" were marked along the trajectory. As described in further detail elsewhere herein, the checkpoints may be marked manually by the user, or they may be marked automatically by the simulator, e.g., by the simulator's processor. In FIG. 7H, an "INSERT&STEER" button 714 is shown on the screen. According to some embodiments, clicking on the "INSERT&STEER" button 714 initiates a simulation stored in the simulator's memory module and/or a local server and/or a remote server and/or cloud, of an instrument being steered according to the preset trajectory. The stored simulation may include a sequence of images obtained from actual previously executed medical procedures According to some embodiments, clicking the "INSERT&STEER" button 714 results in a real-time simulation of instrument steering according to the calculated trajectory. According to some embodiments, the simulation may be executed using a real robot, a real medical instrument and a phantom device. In such embodiments, insertion and steering of the real (tangible) instrument may be initiated by clicking the "INSERT&STEER" button 714.

FIG. 7I is a screenshot of GUI 70 and an animation window 72, which shows an animation of the patient (cross-section of the patient's body) with the robot 770 attached thereto, and a medical instrument 78 inserted toward the target 752 according to the planned trajectory 757 and reaching the first checkpoint 7572'. It can be appreciated, that although an image of the instrument having already reached the first checkpoint is shown in FIG. 7I, the animation may comprise a video of the instrument (i.e., the tip of the instrument) advancing from the entry point to the first checkpoint.

FIG. 7J is a screenshot of GUI 70 following imaging to verify the location of the tip of the instrument 78 after execution of the insertion step, as well as the location of the target 752, i.e., to check if the target remained in its initial location as marked on the image-view, or if it has moved as a result of the forces exerted by the instrument as it was being inserted into the tissue toward the first checkpoint 7572'. According to some embodiments, the user may be prompted to initiate such imaging, which may be referred to as "confirmation scan". According to some embodiments, the presented confirmation scan may be retrieved from the simulator's memory module or from a local or remote server. According to some embodiments, the simulation may be executed using a real robot, instrument and imaging system, together with a phantom device. In such embodiments, actual imaging may be initiated to confirm the actual locations of the instrument and the target within the phantom device. In FIG. 7J, a "CONFIRM" button 716 is shown on the screen. According to some embodiments, the user is required to confirm the locations of the instrument and the target by clicking the "CONFIRM" button 716. According to some embodiments, an instructions window 730 may be presented on the screen during the simulation, to guide and assist the user. In FIG. 7J, for example, the instructions window 730 includes the following instructions: "Click the confirm button to confirm location of the instrument tip and target location".

Once the locations of the instrument and the target are confirmed, advancement of the instrument to the next checkpoint may be resumed. According to some embodiments, advancing the instrument to the next checkpoint may require be executed after the user clicks an "INSERT&STEER" button, as described in FIG. 7H above. FIG. 7K is a screenshot of GUI 70 and animation window 72, showing the medical instrument 78 reaching the third checkpoint 7572'''. According to some embodiments, the instrument advancing from the first checkpoint to the third checkpoint may be a result of the user choosing to cancel/remove the second checkpoint during the simulation. It can be appreciated, that although an image of the instrument having already reached the third checkpoint is shown in FIG. 7K, the animation may comprise a video of the instrument (i.e., the tip of the instrument) advancing from the first checkpoint to the third checkpoint. In the example shown in FIG. 7K, the target 752 has moved from its initial position during and as a result of the advancement of the medical instrument 78 within the tissue. According to some embodiments, the movement of the target is pre-set for the specific simulation case and the animation is pre-recorded to show such movement. According to some embodiments, the simulator includes algorithm(s) which can estimate tissue (and specifically, target) movement resulting from the simulation parameters (e.g., tissue type, selected instrument, calculated trajectory, etc.), and the animation showing movement of the target may be created in real-time. According to some embodiments, the simulation may be executed using a real robot, instrument and imaging system, together with a phantom device, such that actual target movement within the phantom may occur during the simulation, and the animation may be created in real-time based on real-time images obtained from the imaging system.

FIG. 7L is a screenshot of GUI 70 following imaging to verify the location of the tip of the instrument 78 and of the target 752 after execution of the insertion step. As target movement has been detected, the user may be prompted to update the target location and then the trajectory by clicking an "UPDATE" button 718 on the GUI 70. According to some embodiments, the determination of the updated (real-time) location of the target may be performed manually by the user, i.e., the user visually identifies the target in the images and marks the new target position on the GUI. According to some embodiments, the determination of the real-time target location may be performed automatically by the processor using image processing techniques and/or data-analysis algorithm(s). According to such embodiments, the user may be prompted to confirm the updated location as marked by the processor, or edit the updated location. According to some embodiments, once the updated target location has been marked on the image-view, the trajectory is updated accordingly. According to some embodiments, for example embodiments in which the movement of the target is pre-set, the adjusted trajectory may be pre-set accordingly, such that stored images and/or animations showing the updating of the trajectory may be displayed upon the user clicking the "UPDATE" button 718. According to some embodiments, the updated trajectory may be calculated in real-time, based on simulated target movement (i.e., using AI algorithm(s)) or actual target movement (i.e., in case of actual target movement within a phantom). According to some embodiments, the simulator may include AI algorithm(s) which can predict the movement of the target and update the trajectory to facilitate the medical instrument reaching the target at its predicted end-point location.

FIG. 7M is a screenshot of GUI 70 and animation window 72, showing the medical instrument 78 reaching the target 752 at its updated location, following an updated trajectory 757'. As shown in FIG. 7M, due to the update of the trajectory, the instrument reached the target following a non-linear trajectory 757'. It can be appreciated, that although an image of the target and the trajectory having already been updated and the instrument having already reached the target is shown in FIG. 7M, the animation may comprise a video showing the updating of the target location, the updating of the trajectory, and the advancement of the instrument from the third checkpoint to the target. According to some embodiments, in which the movement of the target is pre-set for the specific simulation case, the animation showing the updating of the target location and of the trajectory, and the steering of the instrument according to the updated trajectory until reaching the target may be pre-recorded. According to some embodiments, in which the simulator includes algorithm(s) which can estimate target movement resulting from the simulation parameters, the animation showing the updating of the target location and of the trajectory, and the steering of the instrument according to the updated trajectory until reaching the target may be created in real-time. According to some embodiments, the simulation may be executed using a real robot, instrument and imaging system, together with a phantom device, such that actual target movement with the phantom may occur during the simulation. In such embodiments, the animation may be created in real-time based on target and trajectory updated executed during the simulation session and real-time images obtained from the imaging system.

FIG. 7N is a screenshot of GUI 70 following imaging to verify the location of the tip of the instrument 78 and of the target 752 after execution of the final insertion step. As shown in FIG. 7N, the instrument 78 has successfully reached the target 752.

Algorithms

According to some embodiments, the memory module of the simulator, for example memory module 108 shown in FIG. 1, may be configured to store one or more algorithms configured to generate a graphic user interface (GUI) on a monitor, for example display 104 shown in FIG. 1. According to some embodiments, and as described in greater detail elsewhere herein, the one or more algorithms may be configured to receive data associated with a registration of a user and/or organization. According to some embodiments, the one or more algorithms may be configured to identify a registration failure. According to some embodiments, the one or more algorithms may be configured to alert a user of registration failure upon occurrence. According to some embodiments, the one or more algorithms may be configured to alert a user regarding a detected failure.

According to some embodiments, the one or more algorithms may be configured to display error alerts associated with failure to connect to the memory module, failure to update the memory module, failure to identify a user account, failure to receive data from a user interface module, for example user interface module 106 shown in FIG. 1, and the like.

According to some embodiments, the one or more algorithms may be configured to generate scenarios, which are to be addressed by the user during the simulation session, and alert the user accordingly. Such scenarios may correspond to scenarios which may occur during actual planning and/or executing of a medical instrument insertion and/or steering procedure. Such scenarios, and corresponding error messages, may be, but not limited to: a scan (planning/registration) was not loaded, registration of the automated medical device failed, the planned trajectory is invalid, the trajectory became invalid or too curved during the procedure, instrument detection has failed and respiration synchronization related issues.

According to some embodiments, the GUI may allow the user to respond to the presented scenario/error messages by a plurality of actions. Such action may be, depending on the presented scenario, one or more of: re-positioning of the target, marking new obstacles, removing marked obstacles, changing a position of one or more checkpoints, changing a distance between two or more checkpoints, removing/adding one or more checkpoints, re-sending a scan and/or image, adjusting an image-view (e.g., zoom in, zoom out, shift to left/down/right/up), recalculating the trajectory, and the like. According to some embodiments, the GUI may include an introduction screen and/or instruction screens (choose, select, save, quit, help, and the like). According to some embodiments, the one or more algorithms may be configured to receive user input associated with "help" options, and generate a window and/or text box and/or audio response associated with instructions and/or recommendations relating to the specific current step of the simulation program.

According to some embodiments, the simulator system's memory module may include at least one database of pre-selected images and/or scans, such as, for example, a database of DICOMs. According to some embodiments, the memory module may be configured to receive updates associated with new/additional images, scans and/or animations. According to some embodiments, the updates are automatic. According to some embodiments, the updates are periodic and/or continuous. According to some embodiments, the updates may be associated with clinical procedures and/or data obtained during simulations and/or implementations of the simulator system, the method 30, the method 40, the method 50, and/or in previous procedures. According to some embodiment, and as described in greater detail elsewhere herein, the updates may be manually inputted by a user.

According to some embodiments, the memory module may include one or more robot (automated medical device) modules configured to be superimposed onto one or more images. According to some embodiments, the robot module may include a cut-out robot image. According to some embodiments, the robot module may include a 3D and/or 2D graphic module. According to some embodiments, the robot module may be configured to set a virtual robot in the simulation based, at least in part, on data associated with previous procedures and/or data associated with the position of the robot in scans and/or images stored in the memory module. According to some embodiments, the robot module may be configured to set a virtual robot in the simulation, directly above the selected entry point. According to some embodiments, the robot module may be configured to set a virtual robot in the simulation, parallel to the patient's head-feet axis and/or above the patient's skin.

According to some embodiments, the memory module may include one or more medical instrument modules configured to be superimposed onto one or more DICOMs and/or images. According to some embodiments, the one or more algorithms may be configured to align the medical instrument module in relation to the image-view such that the instrument's top portion is aligned with the end effector of the virtual robot. According to some embodiments, the medical instrument tip of the medical instrument module may be set to have a random lateral error configured to mimic real medical instrument steering behavior. According to some embodiments, the medical instrument tip of the medical instrument module may be set to have a predetermined offset configured to mimic real medical instrument steering behavior. According to some embodiments, the offset and/or the error may vary in accordance with a type of tissue and/or type of procedure in the simulation.

According to some embodiments, the one or more algorithms may be configured to receive one or more labels per image, scan, and/or animation. According to some embodiments, the one or more labels may be associated with one or more possible procedures and/or regions of interest associated with the images, scans, and/or animations within the memory module. According to some embodiments, the one or more labels may be associated with one or more of patient parameters (for example, body type, anatomy, medical history, medical characteristics, etc.), patient positions (for example, prone, supine, etc.), target characteristics (for example, shape, size, condition, etc.).

According to some embodiments, the one or more algorithms may be configured to classify the images, scans, and/or animations as being associated with one or more possible procedures and/or regions of interest. According to some embodiments, the one or more algorithms may be configured to display optional procedures for a user to choose from, wherein the optional procedures are associated with one or more of the classifications and/or the labels of the images, scans, and/or animations within the memory module.

According to some embodiments, the one or more algorithms may be configured to generate recommendations and/or implementations which may enhance further medical procedure simulations or actual clinical procedures. According to some embodiments, the one or more algorithms may be configured to generate instructions and/or recommendations, based, at least in part, on some of the collected primary data (also referred to as "raw data") and/or data derived therefrom ("manipulated data").

According to some embodiments, the output recommendations may include one or more of: determining optimized checkpoint distribution along a trajectory path of the (virtual) medical instrument, recommendation of entry point location, recommendation of "no-fly" zones (obstacles), or combinations thereof. For example, once the user marks the target, the algorithm may generate a recommendation to an entry point, number and position of checkpoints, etc.

According to some embodiments, the generated recommendation and/or operating instructions may include one or more of: clinical related recommendations, optimization of various operating parameters and algorithms, user feedback, performance analysis, or combinations thereof. According to some embodiments, the clinical related recommendations may include one or more of: prediction, prevention and/or early detection of clinical complications (e.g., pneumothorax, internal bleeding, breathing abnormalities, etc.) associated with the parameters of the simulated procedure, as disclosed, for example, in co-owned International Patent Application Publication No. WO 2021/214,751, which is hereby incorporated by reference in its entirety. According to some embodiments the clinical complications include, for example, risk of pneumothorax. A pneumothorax occurs when air enters the pleural sac, i.e., the space between the lung and the chest wall, pushing on the outside of the lung and causing the lung to collapse. Pneumothorax can be a complete lung collapse or a partial lung collapse, and it can inadvertently occur during medical procedures that involve the insertion of a medical instrument (e.g., needle) into the chest, such as lung biopsy. Pneumothorax may be life-threatening, thus it is advantageous to train users to plan and execute an insertion procedure into the chest while avoiding the risk of pneumothorax. According to some embodiments, the simulator may initiate during a simulation session scenarios which may be indicative of the development of pneumothorax, such as enlargement of the pleural cavity volume, certain changes in the patient's respiration patterns, etc. If the user notices the presented indicative symptoms, the user may execute mitigating actions, such as selecting a different entry point, selecting a different medical instrument, repositioning one or more checkpoints, etc. If the user fails to notice the presented indicative symptoms, an alert may be generated (for example, a visual alert displayed on the GUI and/or an auditory notification) informing the user of the risk and allowing him/her to execute mitigating actions thereafter. Alternatively, the simulation may continue until pneumothorax occurs, and the user may then be informed of the indicative symptoms he/she failed to notice. According to some embodiments, such training may utilize AI model(s) which can predict and/or detect the occurrence of pneumothorax, alert the user and, optionally, recommend actions that may prevent the occurrence of pneumothorax or prevent worsening of a developing pneumothorax. The output of such model(s) may be, for example, probability of pneumothorax occurrence, estimated pneumothorax size, potential modifications which could reduce the probability of pneumothorax, and the like, or any combination thereof.

According to some embodiments, the one or more algorithms may be configured to generate one or more animations associated with the advancement of the (virtual) medical instrument between the confirmed checkpoints along the confirmed trajectory. According to some embodiments, the one or more algorithms may be configured to generate and/or obtain one or more DICOMs associated with the simulation of the procedure. According to some embodiments, the one or more algorithms may be configured to show the (virtual) instrument's advancement on the same set of DICOMS. According to some embodiments, the one or more algorithms may be configured to generate the image-views and/or the animations based, at least in part, on one or more images stored in the memory module. According to some embodiments, the one or more algorithms may be configured to generate the image-views and/or the animations based, at least in part, on previously collected and/or accumulated data. Advantageously, having the one or more algorithms generate the image-views and/or the animations based, at least in part, on previously collected and/or accumulated data, allows the simulation to include data associated with tissue and/or target movements during simulation of the advancement of the medical instrument according to the planned trajectory. According to some embodiment, the one or more algorithms may be configured to label and/or classify data of previous simulations. According to some embodiments, the one or more algorithms may be configured to simulate the movement of the tissue in a simulation session, for example, movement resulting from the instrument insertion forces, which may differ even between simulations of the same procedure, depending on the selected entry point, the marked "no-fly" zones, etc.

According to some embodiments, the one or more algorithms may be configured to generate an animation which may include a 2D and/or a 3D presentation of the insertion and/or steering procedure. According to some embodiments, the animation may include the patient preparation. According to some embodiments, the animation may include the preparation of the automated device (e.g., placing the robot on the patient, coupling the medical instrument to the robot, and the like). According to some embodiments, the animation may include one or more procedures performed by the virtual robot. According to some embodiments, the animation may include one or more procedures performed using the virtual medical instrument based, at least in part, on the selected region of interest, procedure type, patient type, target organ, confirmed checkpoints, marked obstacles, and the like. According to some embodiments, the one or more algorithms may be configured to predict and mimic the movement of the medical instrument within the tissue in animations and/or DICOMs.

According to some embodiments, the algorithms may be configured to generate one or more audio messages in accordance with calculations and/or recommendations executed by one or more of the algorithms. According to some embodiments, the audio may include a narration of the simulated procedure step and/or instructions/explanations to the user, such as voiceover audio. According to some embodiments, the audio may include ambient sound effects associated with the simulated medical procedure. According to some embodiments, the audio may include one or more sound effects associated with the machines included in the simulation (e.g., a CT scanner, the robot, and/or the medical instrument). According to some embodiments, the audio may include an audio feature, wherein the audio may be turned on and/or off by a user, e.g., via the user interface module.

According to some embodiments, the one or more algorithms may include supervised and/or unsupervised ML/DL models. According to some embodiments, the ML/DL models may be configured to receive data associated with ongoing simulations and/or completed simulations. According to some embodiments, the one or more ML/DL models may be configured to receive data associated with ongoing simulations and/or completed simulations manually by a user. According to some embodiments, the one or more ML/DL models may be configured to receive data associated with ongoing simulations and/or completed simulations automatically, for example, e.g., via the processor. According to some embodiments, the one or more algorithms may be configured to preprocess and/or normalize the received data. According to some embodiments, the one or more algorithms may be configured to extract features associated with high success rate of the simulation. According to some embodiments, the one or more algorithms may be configured to implement image processing algorithms. According to some embodiments, the ML/DL models may be configured to train using a training set at least partially associated with previous simulations. According to some embodiments, the training set may include the rank score of the simulation. According to some embodiments, the one or more algorithms may be configured to calculate, assess, and/or predict a success level of a simulated procedure during any one of the target selection, entry point selection, obstacle(s) selection, checkpoint selection/confirmation, and the like.

According to some embodiments, the one or more algorithms may be configured to receive data from the user interface module associated with a manually inputted procedure update, a complication update, an obstacle update and/or the like.

According to some embodiments, one or more algorithms may be configured to simulate movement of a tissue during medical procedures involving insertion of various medical instruments. For example, such tissue movement may result or be attributed to the insertion and/or movement of the medical instrument, in particular, along the advancement path thereof. In some embodiments, such movement simulation algorithms may incorporate artificial intelligence capabilities.

User Accounts

According to some embodiments, the method may include receiving data associated with a user account, thereby being configured to track progress of one or more users, a group of users, or a plurality of users associated with one or more organization. According to some embodiments, the method may include ranking the success of procedure simulations completed by the one or more users. According to some embodiments, the method may include applying data inputted by the one or more users to an algorithm configured to extract features and identify optimal selected and/or confirmed parameters of successful procedure simulations.

According to some embodiments, the method may include receiving data and/or user input associated with a specified user account. According to some embodiments, the data may include one or more of a user account, name, code, a group of users, an organization wherein a plurality of users are associated with the organization, and the like. According to some embodiments, the method may include saving data associated with the procedure, wherein the saved data comprises one or more tags associated with the specified user account. According to some embodiments, the one or more algorithms may be configured to allow a user to log into a user account/profile. According to some embodiments, the user account/profile may include tags associated with previous simulations completed (and/or uncompleted) by the user. According to some embodiments, the method may include saving data associated with the simulation of the procedure, wherein the saved data is stored within the specified user account. According to some embodiments, the method may allow pausing a simulation that has begun. According to some embodiments, the method may include saving a paused simulation with one or more tag associated with a user profile, thereby allowing the user to access a previously paused simulation associated with his/her user account. According to some embodiments, the method may enable resuming a paused simulation. Advantageously, a user can therefore be able to log into their user account, start a simulation, pause the simulation, log out, and after a period of time log into their user account and resume the simulation that had been paused. According to some embodiments, the method may enable users to share simulation sessions with other users, either in real-time (i.e., during a simulation) or offline. According to some embodiments, the method may enable users to receive input from other users relating to a specific simulation session, optionally directly on the display of the simulator.

According to some embodiments, the method may include assessing a level of success of the procedure simulation and comparing the assessed level with similar procedure simulations logged and/or associated with the specified user account. According to some embodiments, the method may include applying data associated with a specified user account to an algorithm configured to assess a level of success of the procedure simulation in relation to previous simulations of the same user account and/or the same organization or group (which may include a plurality of user accounts). According to some embodiments, the method may include calculating statistics associated with a specified user account and/or a group of user accounts. According to some embodiments, one or more algorithms may be configured to generate statistics associated with an outcome of one or more procedure simulations of a specified user account, group of user accounts, and/or organization. For example, an organization may include a hospital, wherein each physician of the relevant department/s has a user account associated with the hospital. For example, a group may include a unit or sector of the hospital, wherein the physicians within the unit or sector are associated with the group. According to some embodiments, the method may include analyzing the logged procedures of a specified user account and/or a group of user accounts. According to some embodiments, the selected and/or confirmed parameters of the simulations of each user may be compared with the selected and/or confirmed parameters of the simulations of one or more other users.

According to some embodiments, one or more algorithms are configured to identify and/or extract features associated with successful procedure simulations. According to some embodiments, the one or more algorithms are configured to identify and/or extract features associated with simulations completed by one or more users having a high success rate. For example, in some embodiments, the one or more algorithms are configured to identify patterns and/or features associated with simulations completed by the users having the highest rank scores (e.g. the top 10%). According to some embodiments, the method may include prompting a user to adjust one or more of a target position, an entry point position, obstacle/s position and/or number or position of checkpoints based, at least in part, on analyzed data associated with logged procedure simulations of a specified user account and/or a group of user accounts. According to some embodiments, the method may include prompting a user to adjust one or more of a target position, an entry point position, obstacle/s position and/or number or position of checkpoints based, at least in part, on the extracted and/or identified features.

Training Programs

According to some embodiments, the simulation method includes receiving user input associated with one or more training programs. According to some embodiments, the method may include registering a user account with one or more specified training programs. According to some embodiments, the method includes displaying one or more options associated with one or more training programs. According to some embodiments, the training program may include a specific field of operation, a specific specialty, a specific medical instrument, and/or the like. According to some embodiments, the one or more training programs include one or more procedure options for a user to choose from. According to some embodiments, the one or more training programs include a specific course of one or more pre-determined procedures, procedure types, target organs, and the like.

According to some embodiments, the one or more training programs may include specific requirements associated with a completion of the training program. According to some embodiments, the requirements may include one or more of a number of completed simulations (e.g., at least 5 or at least 10 completed simulations), a number of successfully completed simulations (e.g., in which the rank score of the simulation is at least 9 out of 10), a minimal average of the rank score of the completed simulations, and the like.

According to some embodiments, the one or more training programs may include competitions between two or more users, two or more groups, and/or two or more organizations. According to some embodiments, the competitions may be periodic (e.g., daily, weekly, monthly, and/or yearly). According to some embodiments, the competitions may include procedure simulations of the same type and/or based on the same test cases, image-views and/or scans. For example, according to some embodiments, the competition may be scored based on average time for completion of each simulation, average rank/score of the completed simulations, and number of successfully completed simulations.

According to some embodiments, further provided herein are non-transitory computer readable medium storing computer program instructions for executing the simulation methods, as disclosed herein.

According to some embodiments, further provided herein is computer-readable storage medium having stored therein software, executable by one or more processors for performing the simulation method, as disclosed herein.

According to some embodiments, provided herein are simulator kits which include computer readable instructions for executing the simulation methods as disclosed herein, and an automated medical device.

According to some embodiments, provided herein are simulator kits which include computer readable instructions for executing the simulation methods as disclosed herein, an automated medical device for executing the insertion and/or steering procedure and a phantom which mimics a region of interest of a body of a subject and on which the simulation may be executed using the automated medical device.

According to some embodiments, the kit may further include instructions for using the kit and/or the simulator system, or at least one or more individual modules thereof.

According to some embodiments, the medical instrument being simulated may be any suitable instrument capable of being inserted and steered within the body of the subject, to reach a designated target. According to some embodiments, the medical instrument may be selected from, but not limited to: a needle, probe (e.g., an ablation probe), port, introducer, catheter (such as a drainage needle catheter), cannula, surgical tool, fluid delivery tool, or any other suitable insertable tool configured to be inserted into a subject's body for diagnostic and/or therapeutic purposes.

Embodiments of the methods, systems and devices described above may further include any of the features described in the present disclosure, including any of the features described hereinabove in relation to other methods, systems and devices embodiments.

According to some embodiments, the terms "medical instrument" and "medical tool" may be used interchangeably.

According to some embodiments, the terms "subject" and "patient" may be used interchangeably and may refer either to a human subject or to an animal subject.

According to some embodiments, the terms "simulation", "simulated procedure" and "simulation procedure" may be used interchangeably.

According to some embodiments, the terms "model", "algorithm", "data-analysis algorithm" and "data-based algorithm" may be used interchangeably.

Unless specifically stated otherwise, as apparent from the disclosure, it is appreciated that, according to some embodiments, terms such as "processing", "computing", "calculating", "determining", "estimating", "assessing", "gauging" or the like, may refer to the action and/or processes of a computer or computing system, or similar electronic computing device, that manipulate and/or transform data, represented as physical (e.g. electronic) quantities within the computing system's registers and/or memories, into other data similarly represented as physical quantities within the computing system's memories, registers or other such information storage, transmission or display devices.

The embodiments described in the present disclosure may be implemented in digital electronic circuitry, or in computer software, firmware or hardware, or in combinations thereof. The disclosed embodiments may be implemented as one or more computer programs, i.e., one or more modules of computer program instructions, encoded on computer storage medium for execution by, or to control the operation of, one or more data processing apparatus. Alternatively or in addition, the computer program instructions may be encoded on an artificially generated propagated signal, for example, a machine-generated electrical, optical or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of any one or more of the above. Furthermore, while a computer storage medium is not a propagated signal, a computer storage medium can be a source or destination of computer program instructions encoded in an artificially generated propagated signal. The computer storage medium can also be, or be included in, one or more separate physical components or media (for example, multiple CDs, disks, or other storage devices).

The operations described in the present disclosure can be implemented as operations performed by a data processing apparatus on data stored on one or more computer-readable storage devices or received from other sources.

The terms "processor" and/or "data processing apparatus" as used herein may encompass all types of apparatus, devices, and machines for processing data, including by way of example a programmable processor, a computer, a system on a chip/s, or combinations thereof. The data processing apparatus can include special purpose logic circuitry, for example, an FPGA (field programmable gate array) or an ASIC (application specific integrated circuit). The apparatus can also include, in addition to hardware, code that creates an execution environment for the computer program in question, for example, code that constitutes processor firmware, a protocol stack, a database management system, an operating system, a cross-platform runtime environment, a virtual machine, or combinations thereof. The apparatus and execution environment can realize various different computing model infrastructures, such as web services, distributed computing and grid computing infrastructures.

A computer program (also referred to as a program, software, software application, script or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A computer program can be stored in a portion of a file that holds other programs or data, in a single file dedicated to the program in question, or in multiple coordinated files (for example, files that store one or more modules, sub programs or portions of code). A computer program can be deployed to be executed on one computer or on multiple computers that are located at one site or distributed across multiple sites and interconnected by a communication network.

The processes and logic flows described herein can be performed by one or more programmable processors, executing one or more computer programs to perform actions by operating on input data and generating output. The processes and logic flows can also be performed by, and an apparatus can also be implemented as, special purpose logic circuitry, for example, an FPGA or an ASIC. Processors suitable for the execution of a computer program include both general and special purpose microprocessors, and any one or more processors of any type of digital computer. Generally, a processor will receive instructions and data from a read-only memory or a random access memory or both. The essential elements of a computer are a processor for performing actions in accordance with instructions and one or more memory devices for storing instructions and data. A computer may, optionally, also include, or be operatively coupled to receive data from or transfer data to, or both, one or more mass storage devices for storing data, for example, magnetic, magneto optical discs, or optical discs. Moreover, a computer can be embedded in another device, for example, a mobile phone, a tablet, a personal digital assistant (PDA, a game console, a Global Positioning System (GPS) receiver, or a portable storage device (for example, a USB flash drive). Devices suitable for storing computer program instructions and data include all forms of non-volatile memory, media and memory devices, including semiconductor memory devices, for example, EPROM, EEPROM, random access memories (RAMs), including SRAM, DRAM, embedded DRAM (eDRAM) and Hybrid Memory Cube (HMC), and flash memory devices; magnetic discs, for example, internal hard discs or removable discs; magneto optical discs; read-only memories (ROMs), including CD-ROM and DVD-ROM discs; solid state drives (SSDs); and cloud-based storage. The processor and the memory can be supplemented by, or incorporated in, special purpose logic circuitry.

The processes and logic flows described herein may be performed in whole or in part in a cloud computing environment. For example, some or all of a given disclosed process may be executed by a secure cloud-based system comprised of co-located and/or geographically distributed server systems. The term "cloud computing" is generally used to describe a computing model which enables on-demand access to a shared pool of computing resources, such as computer networks, servers, software applications, and services, and which allows for rapid provisioning and release of resources with minimal management effort or service provider interaction.

Aspects of the disclosure may be described in the general context of computer-executable instructions, such as program modules, being executed by a computer. Generally, program modules include routines, programs, objects, components, data structures, and so forth, which perform particular tasks or implement particular abstract data types. Disclosed embodiments may also be practiced in distributed computing environments where tasks are performed by remote processing devices that are linked through a communications network. In a distributed computing environment, program modules may be located in both local and remote computer storage media including memory storage devices.

In the description and claims of the application, the words "include" and "have", and forms thereof, are not limited to members in a list with which the words may be associated.

Unless otherwise defined, all technical and scientific terms used herein have the same meaning as commonly understood by one of ordinary skill in the art to which this disclosure pertains. In case of conflict, the patent specification, including definitions, governs. As used herein, the indefinite articles "a" and "an" mean "at least one" or "one or more" unless the context clearly dictates otherwise.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. No feature described in the context of an embodiment is to be considered an essential feature of that embodiment, unless explicitly specified as such.

Although steps of methods according to some embodiments may be described in a specific sequence, methods of the disclosure may include some or all of the described steps carried out in a different order. The methods of the disclosure may include a few of the steps described or all of the steps described. No particular step in a disclosed method is to be considered an essential step of that method, unless explicitly specified as such.

The phraseology and terminology employed herein are for descriptive purpose and should not be regarded as limiting. Citation or identification of any reference in this application shall not be construed as an admission that such reference is available as prior art to the disclosure. Section headings are used herein to ease understanding of the specification and should not be construed as necessarily limiting.

What is claimed is:

1. A method for simulation of planning and executing a procedure for robotic insertion and/or steering of a medical instrument toward an internal target, for training a user, the simulation method comprising:

displaying a plurality of medical procedure options;

receiving user input associated with a selected medical procedure;

displaying one or more images of a region of interest associated with the selected medical procedure;

receiving user input associated with a location of at least one of a target and an entry point on the one or more images;

receiving user input associated with locations of one or more obstacles between the entry point and the target;

displaying on the one or more images a trajectory from the entry point to the target, the trajectory being calculated in real-time by applying at least one of the selected medical procedure, the target, the entry point and the one or more obstacles to a data-analysis algorithm;

displaying one or more checkpoints along the trajectory, wherein one or more default checkpoints are automatically marked and the user is prompted to confirm the default checkpoints or to change a number and/or locations of the displayed checkpoints;

receiving user input regarding initiation of advancement of the medical instrument to a next checkpoint along the trajectory;

prompting the user to initiate imaging after the advancement to the next checkpoint to verify a location of the medical instrument and a current location of the target;

receiving confirmation input confirming the location of the medical instrument and the current location of the target; and in response to the confirmation input, displaying on the one or more images advancement of the medical instrument according to the trajectory, from the next checkpoint to a subsequent checkpoint or to the target; thereby training the user in planning and executing a procedure for robotic insertion and/or steering of a medical instrument.

2. The simulation method of claim 1, comprising:

determining, by a processor, if the received user input associated with the location of the at least one of the target and the entry point is valid and/or optimal;

if the processor determines that the received user input associated with the location of the at least one of the target and the entry point is invalid and/or not optimal, displaying on the one or more images a valid and/or optimal location of the at least one of the target and the entry point;

determining if the received user input associated with the locations of the one or more obstacles is valid and/or optimal; and if it is determined by the processor that the received user input associated with the locations of the one or more obstacles is invalid and/or not optimal, displaying on the one or more images valid and/or optimal locations of the one or more obstacles.

3. The simulation method of claim 1, comprising receiving user input associated with a type of the medical instrument for use in the simulation;

determining, by a processor if the received user input associated with the type of medical instrument for use in the simulation is optimal; and if it is determined by the processor that the received user input associated with the type of medical instrument for use in the simulation is not optimal, recommending to the user an optimal type of medical instrument for use in the simulation.

4. The simulation method of claim 1, comprising receiving user input associated with locations of one or more checkpoints along the trajectory;

determining, by a processor if the received user input associated with the locations of the one or more checkpoints is valid and/or optimal; and if it is determined by the processor that the received user input associated with the locations of the one or more checkpoints is invalid and/or not optimal, displaying on the one or more images valid and/or optimal locations of the one or more checkpoints.

5. The simulation method of claim 1, wherein displaying the trajectory and/or displaying the advancement of the medical instrument comprises:

applying at least one of the selected medical procedure, the target, the entry point, the one or more obstacles, the trajectory, and the one or more checkpoints to a data-analysis algorithm configured to output data associated therewith;

obtaining the output of the data-analysis algorithm; and generating a display based, at least in part, on the obtained output, and issuing notifications to assist and/or guide the user during the simulation.

6. The simulation method of claim 5, comprising calculating the trajectory in real-time.

7. The simulation method of claim 1, comprising prompting the user to choose one or more parameters associated with a virtual subject undergoing the simulated procedure;

displaying respiratory activity of the virtual subject, and prompting the user to synchronize one or more of initiating imaging and initiating the advancement of the medical instrument with a point or a phase of a respiratory cycle of the virtual subject.

8. The simulation method of claim 1, comprising displaying movement of the target during the simulation, and displaying an updated trajectory on the one or more images.

9. The simulation method of claim 8, wherein the movement of the target is simulated using one or more data-analysis algorithms.

10. The simulation method of claim 1, wherein the robotic medical device is configured to steer the medical instrument toward the target in a non-linear trajectory.

11. The simulation method of claim 1, comprising assessing a level of success of the simulation.

12. The simulation method of claim 1, comprising updating a database with data associated with a completed simulation; and saving data associated with the simulation, wherein the saved data comprises one or more tags associated with a specified user account and wherein the saved data is stored within the specified user account.

13. The simulation method of claim 1, comprising displaying animation segments during the simulation, the animation segments visualizing one or more of the planning of the simulated procedure and the execution of the simulated procedure; and simulating one or more symptoms indicative of at least one of development and occurrence of a clinical complication.

14. A method for simulation of planning and executing a procedure for robotic insertion and/or steering of a medical instrument toward an internal target, for training a user, the simulation method comprising:

displaying a plurality of medical procedure options;

receiving user input associated with a selected medical procedure;

displaying one or more images of a region of interest associated with the selected medical procedure;

receiving user input associated with a location of at least one of a target and an entry point on the one or more images;

receiving user input associated with locations of one or more obstacles between the entry point and the target;

calculating, in real-time by a processor executing a data-analysis algorithm, a trajectory from the entry point to the target, based on one or more of: the target, the entry point, the one or more obstacles;

displaying on the one or more images the trajectory from the entry point to the target;

displaying one or more checkpoints along the trajectory, wherein one or more default checkpoints are automatically marked, and prompting the user to confirm the one or more default checkpoints or to change a number and/or locations of the displayed one or more checkpoints;

receiving user input requesting advancement of the medical instrument according to the trajectory to a next checkpoint along the trajectory displaying, on the one or more images, advancement of the medical instrument according to the trajectory to the next checkpoint;

prompting the user to initiate imaging after the medical instrument has advanced to the next checkpoint to verify a location of the medical instrument and a current location of the target;

receiving confirmation input confirming the location of the medical instrument and the current location of the target;

in response to the confirmation input, displaying, on the one or more images, advancement of the medical instrument according to the trajectory from the next checkpoint to a subsequent checkpoint or to the target; and simulating on the one or more images the insertion and/or steering of the medical instrument by a robotic medical device, thereby training the user.

15. The simulation method of claim 14, comprising presenting to the user one or more first parameters relating to selection of an optimal location for the at least one of the target and the entry point, and presenting to the user one or more second parameters relating to marking of optimal locations of the one or more obstacles.

16. The simulation method of claim 14, comprising receiving user input associated with a type of medical instrument for use in the simulation, and receiving user input associated with locations of one or more checkpoints along the trajectory.

17. The simulation method of claim 16, comprising presenting to the user one or more third parameters relating to selection of an optimal type of medical instrument for use in the simulation; and presenting to the user one or more fourth parameters relating to optimal locations of the one or more checkpoints along the trajectory.

18. The simulation method of claim 14, comprising simulating movement of the target using one or more data-analysis algorithms, and calculating an updated trajectory in real-time.

19. The simulation method of claim 14, comprising presenting to the user one or more limitations of the robotic medical device to consider during the simulation.

20. The simulation method of claim 14, comprising assessing a level of success of the simulation.

* * * * *